(12) United States Patent
Srivastava et al.

(10) Patent No.: US 12,299,872 B2
(45) Date of Patent: May 13, 2025

(54) DETECTING AND TRACKING MACULAR DEGENERATION

(71) Applicant: Welch Allyn, Inc., Skaneateles Falls, NY (US)

(72) Inventors: Varad Srivastava, Skaneateles, NY (US); Allen R. Hart, Knoxville, TN (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 550 days.

(21) Appl. No.: 17/346,454

(22) Filed: Jun. 14, 2021

(65) Prior Publication Data

US 2021/0390692 A1    Dec. 16, 2021

Related U.S. Application Data

(60) Provisional application No. 63/039,665, filed on Jun. 16, 2020.

(51) Int. Cl.
| | |
|---|---|
| *G06T 7/11* | (2017.01) |
| *G06T 5/40* | (2006.01) |
| *G06T 7/00* | (2017.01) |
| *G06T 7/136* | (2017.01) |
| *G06T 7/62* | (2017.01) |

(52) U.S. Cl.
CPC .............. *G06T 7/0012* (2013.01); *G06T 5/40* (2013.01); *G06T 7/11* (2017.01); *G06T 7/136* (2017.01); *G06T 7/62* (2017.01); *G06T 2207/30041* (2013.01)

(58) Field of Classification Search
None
See application file for complete search history.

(56) References Cited

U.S. PATENT DOCUMENTS

| | | | |
|---|---|---|---|
| 2011/0242306 A1* | 10/2011 | Bressler | A61B 3/0025 382/128 |
| 2011/0299034 A1 | 12/2011 | Walsh | |
| 2012/0237096 A1 | 9/2012 | Tobin et al. | |

(Continued)

FOREIGN PATENT DOCUMENTS

| | | |
|---|---|---|
| WO | WO2008077412 A1 | 7/2008 |
| WO | WO2018069768 A2 | 4/2018 |

OTHER PUBLICATIONS

Akram, et al, "Automated Drusen Segmentation in Fundus Images for Diagnosing Age Related Macular Degeneration", 2013 International Conference on Electronics, Computer and Computation, Nov. 7, 2013, pp. 17-20.

(Continued)

*Primary Examiner* — Rinna Yi
(74) *Attorney, Agent, or Firm* — Lee & Hayes, P.C.

(57) ABSTRACT

A system includes a vision screening device having at least one sensor. The system also includes a controller operably connected to the at least one sensor. The controller is configured to cause the at least one sensor to obtain an image of an eye, and to identify a region of interest associated with a macula of the eye. The controller is also configured to identify drusen disposed proximate the macula, and to generate an augmented image of the eye. The augmented image includes a component indicating the drusen.

24 Claims, 17 Drawing Sheets

(56) References Cited

U.S. PATENT DOCUMENTS

| | | | | |
|---|---|---|---|---|
| 2014/0152957 | A1* | 6/2014 | Reisman | G06T 7/0012 |
| | | | | 351/246 |
| 2015/0042951 | A1* | 2/2015 | Stanga | A61B 3/12 |
| | | | | 351/206 |
| 2015/0125052 | A1* | 5/2015 | Wong | G06V 10/50 |
| | | | | 382/128 |
| 2016/0307341 | A1* | 10/2016 | Sato | G06T 3/067 |
| 2018/0055574 | A1* | 3/2018 | Krimsky | A61B 34/25 |
| 2018/0092530 | A1* | 4/2018 | Hart | A61B 3/0075 |
| 2018/0289258 | A1* | 10/2018 | Imamura | A61B 3/102 |
| 2019/0180437 | A1* | 6/2019 | Manela | A61B 3/12 |
| 2021/0279874 | A1* | 9/2021 | Boyd | A61B 5/0013 |
| 2021/0304363 | A1* | 9/2021 | Makihira | G06T 11/001 |
| 2021/0386285 | A1* | 12/2021 | Walsh | A61B 5/0066 |

OTHER PUBLICATIONS

Extended European Search Report mailed Oct. 18, 2021 for European Patent Application No. 21179649.5. 14 pages.

Garcia-Floriano, et al., "A machine learning approach to medical image classification: Detecting age-related macular degeneration in fundus images", Computers and Electrical Engineering, vol. 75, Dec. 31, 2017, pp. 218-229.

Porter, Daniel, "What are Drusen", May 23, 2019, retrieved on Feb. 4, 2020 from <https://www.aao.org/eye-health/diseases/what-are-drusen>, 6 pages.

European Office Action mailed Nov. 22, 2023 for European Application No. 21179649.5, a foreign counterpart to U.S. Appl. No. 17/346,454, 7 pages.

* cited by examiner

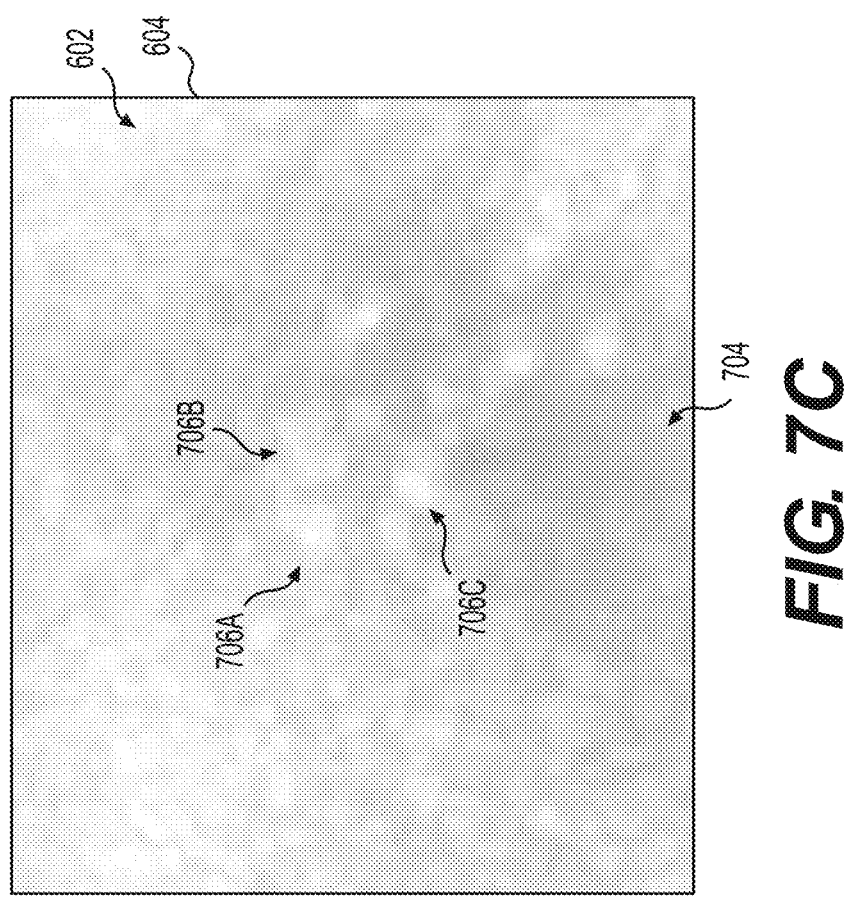

DETECTING AND TRACKING MACULAR DEGENERATION

CROSS-REFERENCE TO RELATED APPLICATIONS

This application is a nonprovisional of, and claims priority to, U.S. Provisional Application No. 63/039,665, filed Jun. 16, 2020, the entire disclosure of which is incorporated herein by reference.

TECHNICAL FIELD

This application is directed to medical equipment, and in particular, to systems and methods associated with detecting and tracking macular degeneration.

BACKGROUND

Vision screening in children and adults typically includes one or more tests or other evaluation procedures to determine various deficiencies associated with the patient's eyes. Such evaluation procedures may include, for example, refractive error tests, convergence tests, accommodation tests, visual acuity tests, macular degeneration examinations, and the like. While one or more of the above procedures may be related, each procedure has a respective purpose. For instance, visual acuity testing typically relies on a person reading characters printed on a Snellen chart at a given distance. That person's visual acuity is based on which size of characters on the chart the person can discern. In a refractive error test, on the other hand, a screening device can be used to direct light onto the person's retinas. Sensors on the device may then collect corresponding light that is reflected by the retinas, and the device may determine a refractive error of each retina based on characteristics of the reflected light. Further, in a macular degeneration examination a screening device may be used to obtain one or more images of the eye. For instance, after dilating the pupil, an ophthalmologist may focus light through the patient's pupil, and may capture images of various portions of the eye to identify the presence of drusen, a key indicator of age-related macular degeneration.

While various screening devices exist, such devices are typically tailored for performing the visual acuity and/or refractive error testing procedures noted above. Such devices are not, however, optimized for the detection and tracking of macular degeneration. For instance, such devices are typically not configured to process images of the eye in order to identify soft drusen disposed beneath the retina. Additionally, such devices are typically not configured to assist ophthalmologists or other healthcare professionals with monitoring the location, size, color, and/or other characteristics of drusen over time. As a result, evaluation procedures performed using existing vision screening devices may lack accuracy, and the early onset of macular degeneration or other eye diseases may go undetected.

The various examples of the present disclosure are directed toward overcoming one or more of the deficiencies noted above.

SUMMARY

In an example of the present disclosure, a system includes a vision screening device having at least one sensor. The system also includes a controller operably connected to the at least one sensor. The controller is configured to cause the at least one sensor to obtain an image of an eye, and to identify, based at least in part on the image, a region of interest associated with a macula of the eye. The controller is further configured to identify, based at least in part on the image, drusen disposed proximate the macula. The controller is also configured to determine a value indicative of a characteristic of the drusen, and to generate an alert based at least in part on the value exceeding a threshold.

In another example of the present disclosure, a system includes a vision screening device having a display and an image capture device. The system also includes a controller operably connected to the display and the image capture device. The controller is configured to cause the image capture device to obtain an image of an eye, and to identify, based at least in part on the image, an optic disc of the eye. The controller is also configured to identify, based at least in part on a characteristic of the optic disc, a region of interest associated with a macula of the eye. The controller is further configured to identify, based at least in part on the image, drusen disposed proximate the macula. In addition, the controller is configured to generate an augmented image of the eye, the augmented image including a component indicating the drusen. The controller is further configured to cause the display to display the augmented image.

In still another example of the present disclosure, a method includes receiving, with a controller, an image of an eye. The method also includes identifying, with the controller and based at least in part on the image, an optic disc of the eye, and identifying, with the controller and based at least in part on identifying the optic disc, a region of interest associated with a macula of the eye. The method further includes identifying, with the controller and based at least in part on the image, drusen disposed proximate the macula. The method also includes generating, with the controller, an augmented image of the eye, the augmented image including a component indicating the drusen.

In a further example of the present disclosure, a system includes a controller, and memory storing instructions which, when executed by the controller, cause the controller to perform operations. Such operations include receiving an image of an eye, and identifying, based at least in part on the image, a region of interest associated with a macula of the eye. Such operations also include identifying, based at least in part on the image, drusen disposed proximate the macula.

BRIEF DESCRIPTION OF THE DRAWINGS

Features of the present disclosure, its nature, and various advantages, may be more apparent upon consideration of the following detailed description, taken in conjunction with the accompanying drawings.

FIG. 7C illustrates yet another example image of the region of interest.

In the figures, the left-most digit(s) of a reference number identifies the figure in which the reference number first appears. The use of the same reference numbers in different figures indicates similar or identical items or features. The drawings are not to scale.

DETAILED DESCRIPTION

The present disclosure is directed to, in part, a vision screening system and corresponding methods. Such an example vision screening system may be configured to perform one or more tests or other evaluation procedures to determine the health of the patient's eyes. For example, the vision screening system may generate one or more graphical representations, such as a series of characters (e.g., a Snellen chart), images, or other items useful for testing the visual acuity of the patient. The system may also generate one or more beams of radiation, and may be configured to direct such beams at the retinas of the patient. The system may collect corresponding light that is reflected back from the retinas, and may determine a refractive error of the patient's eyes based at least in part on characteristics of the collected light. Moreover, the system may be configured to focus light through the patient's pupils while the pupils are dilated, and may be configured to capture images of various portions of the eye. The system may be configured to process the captured images to identify drusen disposed at various locations proximate the retinas, and may also be configured to store information indicative of the number, location, shape, size, color, and/or other characteristics of the drusen. As a result, the systems of the present disclosure may assist in tracking the presence of drusen in the patient's eyes, and may be useful in monitoring the onset and/or progression of macular degeneration over time.

Additional details pertaining to the above-mentioned systems and evaluation procedures are described below with reference to FIGS. 1-10. It is to be appreciated that while these figures describe example systems and devices that may utilize the claimed methods, the methods, processes, functions, operations, and/or techniques described herein may apply equally to other devices, systems, and the like.

Figure 1:
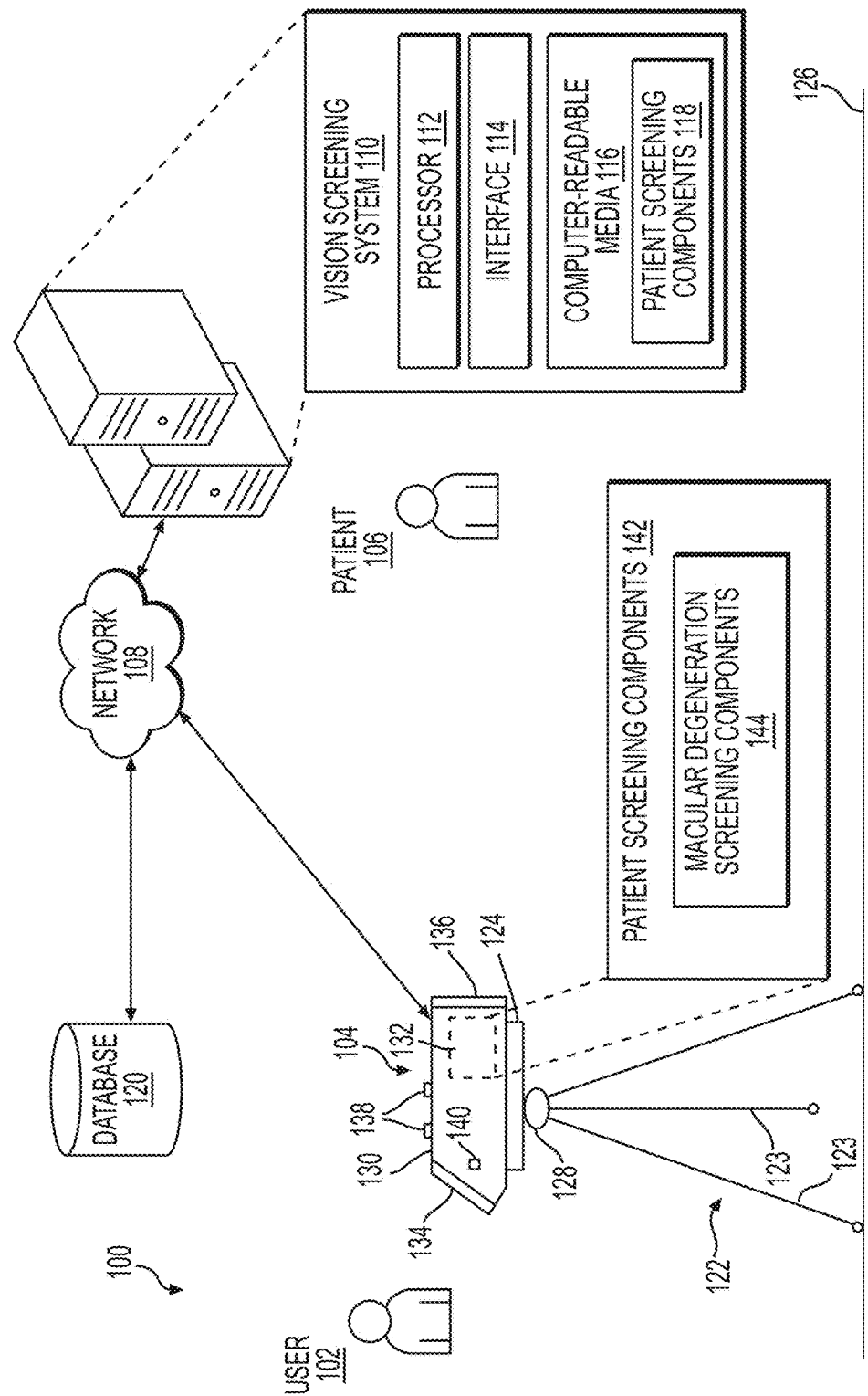
FIG. 1 illustrates an example system of the present disclosure. In some implementations, components of the example system shown in FIG. 1 may be used to perform one or more evaluation procedures associated with detecting macular degeneration.

FIG. 1 illustrates an example system 100 configured to assist in performing various vision screening tests and/or other evaluation procedures. As illustrated in FIG. 1, a user 102 may utilize a vision screening device 104 and/or other components of the system 100 to administer a vision screening test or other evaluation procedure on a patient 106 to determine the health of the patient's eyes. As described herein, the vision screening device 104 may perform one or more evaluation procedures to obtain one or more images of the patient's eyes and/or to determine one or more measurements associated with the patient 106. The vision screening device 104 may provide the images and/or measurements, via a network 108, to a local or remote vision screening system 110 for analysis. In response, the vision screening system 110 may analyze the images and/or measurements to diagnosis the vision health of the patient 106. It should be understood that, while FIG. 1 depicts the system 100 including a single vision screening system 110, in additional examples, the system 100 may include any number of local or remote vision screening systems substantially similar to the vision screening system 110, and configured to operate independently and/or in combination, and configured to communicate via the network 108. In examples, the vision screening system 110 may include one or more processors 112, one or more network interfaces 114, and/or computer-readable media 116. The computer-readable media 116 may store one or more programs, modules, engines, instructions, algorithms, and/or other patient screening components 118 that are executable by the processor(s) 112. Such components of the vision screening system 110 may include, for example, one or more image processing engines, object identification engines, or other components configured to process the images obtained by the vision screening device 104 to assist in performing a macular degeneration screening or other evaluation procedure.

In examples, the vision screening device 104 may comprise a stationary or portable device configured to perform one or more vision screening tests on the patient 106. For example, the vision screening device 104 may be configured to perform a visual acuity test, a refractive error test, an accommodation test, dynamic eye tracking tests, a macular degeneration screening, and/or any other vision screening tests configured to evaluate and/or diagnose the vision health of the patient 106. Although FIG. 1 illustrates a generic vision screening device 104, in some examples, the vision screening device 104 of the present disclosure may comprise an ophthalmoscope or other medical device configured to assist in inspecting and/or otherwise evaluating the retina and other parts of the eye. For instance, in some examples, the vision screening device 104 may comprise a Retina-Vue® 700 Imager or other retinal camera manufactured by Welch Allyn, Inc.®. Due to its stationary or portable (e.g., handheld) nature, the vision screening device 104 may perform the vision screening tests at any location, from conventional screening environments, such as schools and medical clinics, to physician's offices, hospitals, eye care facilities, and/or other remote and/or mobile locations.

As described herein, the vision screening device 104 and/or vision screening system 110 may be configured to perform accommodation and refractive error testing on the patient 104. For example, refractive error and accommodation testing may include displaying a visual stimulus, such as a light or graphical representation, configured to induce a strain to the patient's 104 eyes. In response, the vision screening device 104 may detect the pupils and/or lenses of the eyes of the patient 104, acquire images and/or video data of the pupils/lenses, and the like, and may transmit the vision screening data, via the network 108, to the vision screening system 110 for analysis. Alternatively, or in addition, the vision screening device 104 may perform the analysis locally.

In examples, the vision screening device 104 may also be configured to perform visual acuity testing and/or dynamic eye tracking tests. For example, the vision screening device 104 and/or the vision screening system 110 may be configured to perform visual acuity testing, which includes determining an optotype, determining a distance of the patient 106 from the vision screening device 104, and/or displaying a static or dynamic optotype to the patient 104. The dynamic eye tracking test may include generating a graphical representation, such as a graphic scene or text, for display to the patient 106 and monitoring the movement of the eye, acquire images and/or video data of the eyes, and the like, and may transmit the vision screening data, via the network 108, to the vision screening system 110 for analysis. Alternatively, or in addition, in some examples, the vision screening device 104 may analyze the vision screening data locally.

Moreover, as will be described in greater detail below, the vision screening device 104 may be configured to perform one or more macular degeneration screenings or other like procedures. For example, the vision screening device 104 and/or the vision screening system 110 may be configured to obtain images of portions of the patient's eyes while the patient's pupils are dilated. Such portions may include the macula, the fovea, the optic disc, and/or other structures of the retina. The vision screening device 104 may transmit the captured images, via the network 108, to the vision screening system 110 for analysis. Alternatively, or in addition, in some examples, the vision screening device 104 may analyze the captured images and/or other information locally.

In examples, a memory associated with the vision screening device 104 and/or one or more of the patient screening components 118 (e.g., the computer-readable media 116) may be configured to store and/or access data associated with the patient 106. For example, the patient 106 may provide data (referred to herein as "patient data") upon initiating a vision screening test. For instance, when the vision screening device 104 and/or vision screening system 110 initiates a vision screening test, the patient 106 may provide, or the user 102 may request, patient data including the patient's demographic information, physical characteristics, preferences, and the like. For example, the patient 106 may provide demographic information such as name, date of birth, eye color, ethnicity, gender, and the like. The patient 106 may also provide physical characteristic information such as height of the patient 106. In such examples, the user 102 may request the patient data while the screening is in progress, or before the screening has begun. In some examples, the user 102 may be provided with predetermined categories associated with the patient 106, such as predetermined age ranges (e.g., six to twelve months, one to five years old, etc.), and may request the patient data in order to select the appropriate category associated with the patient 106. In other examples, the user 102 may provide a free form input associated with the patient data. In still further examples, an input element may be provided to the patient 106 directly.

The vision screening device 104 may be configured to capture and/or otherwise obtain image and/or video data associated with the patient 106 at the onset of the vision screening test. For example, the vision screening device 104 may include one or more digital cameras, motion sensors, proximity sensors, or other image capture devices configured to collect any of the images and/or video of the patient 106 described herein, and one or more processors of the vision screening device 104 may analyze the collected images and/or video to determine any of the parameters described herein associated with a macular degeneration screening or other vision screening procedure. Additionally or alternatively, as noted above, the vision screening device 104 may transmit the captured images, via the network 108, to the vision screening system 110 for analysis.

In any such examples, the vision screening system 110 may store such information in the computer-readable media 116 and/or in an external database 120. For example, the database 120 may comprise memory or other computer-readable media substantially similar to and/or the same as the computer-readable media 116. The database 120 may be accessible by the vision screening system 110, and/or by the vision screening device 104, via the network 108. In any such examples, the database 120 may be configured to store the one or more images described herein, the results of various vision screening tests, and/or other patient data in association with a patient ID (e.g., a name, social security number, an alphanumeric code, etc.) or other unique patient identifier. When the user 102 and/or patient 106 enters the patient ID, the patient screening component 118 may access or retrieve the one or more images, the results of various vision screening tests, previous diagnosis, and/or other patient data stored in association with the patient ID. In this way, the results of, for example, multiple macular degeneration screenings may be stored in association with the patient ID over time. Accordingly, in some examples, changes in the number, shape, size, location, hue, and/or other characteristics of drusen identified in the patient's eye can be monitored over time, and the onset and/or progress of macular degeneration can be more clearly understood.

As used herein, the network 108 is typically any type of wireless network or other communication network known in the art. Examples of network 108 include the Internet, an intranet, a wide area network (WAN), a local area network (LAN), and a virtual private network (VPN), cellular network connections and connections made using protocols such as 802.11a, b, g, n and/or ac. U.S. Pat. No. 9,237,846, filed Feb. 17, 2012, describes systems and methods for photo refraction ocular screening and that disclosure is hereby incorporated by reference in its entirety.

As described herein, a processor, such as processor(s) 112, can be a single processing unit or a number of processing units, and can include single or multiple computing units or multiple processing cores. The processor(s) 112 can be implemented as one or more microprocessors, microcomputers, microcontrollers, digital signal processors, central processing units, state machines, logic circuitries, and/or any devices that manipulate signals based on operational instructions. For example, the processor(s) 112 can be one or more hardware processors and/or logic circuits of any suitable type specifically programmed or configured to execute the algorithms and processes described herein. The processor(s) 112 can be configured to fetch and execute computer-readable instructions stored in the computer-readable media 116, which can program the processor(s) 112 to perform the functions described herein.

The network interface(s) 114 may enable wired and/or wireless communications between the components and/or devices shown in system 100 and/or with one or more other remote systems, as well as other networked devices. For instance, at least some of the network interface(s) 114 may include a personal area network component to enable communications over one or more short-range wireless communication channels. Furthermore, at least some of the network interface(s) 114 may include a wide area network component to enable communication over a wide area network. Such network interface(s) 114 may enable, for example, communication between the vision screening system 110 and the vision screening device 104 and/or other components of the system 100, via the network 108.

The computer-readable media 116 may can include volatile and nonvolatile memory and/or removable and non-removable media implemented in any type of technology for storage of information, such as computer-readable instructions, data structures, program modules, or other data. Such computer-readable media 116 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. The computer-readable media 116 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 116 can be used to store any number of functional components that are executable by the processor(s) 112. In many implementations, these functional components comprise instructions or programs that are executable by the processor(s) 112 and that, when executed, specifically configure the one or more processor(s) 112 to perform the actions associated with one or more vision tests.

With continued reference to FIG. 1, in some examples the system 100 may include one or more components (e.g., a base 122) configured to support the vision screening device 104 during use. For example, as shown in FIG. 1, an example base 122 may include two or more legs 123 movably connected to a mount 128. As shown in FIG. 1, in some examples the base 122 may comprise a tripod, and the mount 128 may comprise a substantially rigid frame or other housing associated with the base 122. In such examples, a first end of each leg 123 may be hingedly, pivotably, or otherwise movably connected to the mount 128. Additionally, a second end of each leg, opposite the respective first end, may be configured to be supported by a support surface 126. As illustrated in FIG. 1, in some examples, the support surface 126 may comprise a substantially horizontal support surface 126 configured to support the base 122 and/or other components of the system 100. For instance, the support surface 126 may comprise a floor or other surface of a healthcare facility, screening center, or other location in which one or more components of the system 100 are disposed. Further, in some examples, one or more of the legs 123 may have a fixed length, while in other examples, each of the legs 123 may be extendable or may otherwise have a length that is adjustable in order to dispose the mount 128 and/or components of the system 100 supported by the base 122 at any desired vertical height above the support surface 126.

In any of the examples described herein, the system 100 may further include one or more brackets, rails, joints, fittings, and/or other couplings 124 configured to removably connect a housing 130 of the vision screening device 104 with the mount 128. In such examples, the coupling 124 may include one or more first components (e.g., brackets, protrusions, flanges, rails, etc.) connected to, formed by, and/or otherwise extending from the housing 130 of the vision screening device 104. The coupling 124 may also include one or more second components (e.g., brackets, grooves, ridges, slots, holes, etc.) configured to accept, cooperate with, and/or otherwise mate with such first components in order to facilitate a removable connection between the housing 130 of the vision screening device 104 and the mount 128. In any of the embodiments described herein, such components of the coupling 124 may comprise components of the housing 130 and/or components of the mount 128.

The housing 130 of the vision screening device 104 may comprise a substantially rigid, substantially hollow structure or frame defining an inner space within which one or more display components, control components, sensing components, power supplies, or other components of the system 100 may be located or supported. For instance, the vision screening device 104 may include one or more controllers 132 disposed within the inner space of the housing 130. The vision screening device 104 may further include one or more displays (e.g., a first display 134, a second display 136, etc.) at least partly disposed within and/or supported by the housing 130. The vision screening device 104 may also include various controls 138 operably connected to the controller 132, and/or one or more digital cameras, video cameras, image capture devices, and/or other sensors 140 operably connected to the controller 142. Moreover, as will be described in greater detail below, an example vision screening device 104 may further include one or more additional or alternate components. In any of the examples described herein, the controller 132 and/or other components of the vision screening device 104 may be at least partly disposed within, supported by, and/or otherwise connected to the housing 130.

In some examples, the controller 132 of the vision screening device 104 may be substantially similar to one or more components of the vision screening system 110 described above. For example, the controller 132 of the vision screening device 104 may comprise one or more processors and/or other hardware and/or software components configured to operably control the first display 134, the second display 136, the one or more sensor 140, and/or other components of the vision screening device 104. For instance, the controller 132 may include a single processing unit (e.g., a single processor) or a number of processing units (e.g., multiple processors), and can include single or multiple computing units or multiple processing cores. The processor(s) of the controller 132 can be implemented as one or more microprocessors, microcomputers, microcontrollers, digital signal processors, central processing units, state machines, logic circuitries, and/or any devices that manipulate signals based on operational instructions. For example, the processor(s) of the controller 132 can be one or more hardware processors and/or logic circuits of any suitable type specifically programmed or configured to execute the algorithms, operations, and methods described herein. The processor(s) of the controller 132 can be configured to access, retrieve, and/or execute computer-readable instructions stored in the computer-readable media 116, which can program the processor(s) of the controller 132 to perform the functions described herein. Additionally or alternatively, the processor(s) of the controller 132 can be configured to access, retrieve, and/or execute computer-readable instructions stored in computer-readable media and/or other memory of/local to the vision screening device 104. For example, computer-readable media local to the vision screening device 104 may store one or more programs, modules, engines, instructions, algorithms, and/or other patient screening components 142 similar to and/or the same as the patient screening components 118 described above with respect to the vision screening system 110. In such examples, the patient screening components 142 of the vision screening device 104 may be executable by the controller 132 to perform any of the operations described herein with respect to various vision screening. Such patient screening components 142 of the vision screening device 104 may include, for example, one or more macular degeneration screening components 144 tailored to assist in performing operation of a macular degeneration screening on the patient 106. For instance, such macular degeneration screening components 144 may comprise one or more image capture engines, image processing engines (e.g., segmentation engines, thresholding engines, blurring engines, object identification engines, image augmentation engines, or other components configured to process the images obtained by the vision screening device 104, and to otherwise assist in performing a macular degeneration screening. Such macular degeneration screening components 144 may comprise software and/or hardware components of the vision screening device 104.

In any of the examples described herein, the controller 132 may comprise one or more processors configured to receive various information, signals, and/or other inputs from one or more controls 138 of the vision screening device 104. In some examples, the controls 138 may receive such inputs from the user 102 during operation of the system 100, and one or more such inputs may comprise a command or a request for the vision screening device 104 to generate, display, provide, and/or otherwise output one or more Snellen charts, characters, or other images included in a visual acuity examination or other vision test. One or more such inputs may also comprise a command or a request for the vision screening device 104 to generate, display, provide, and/or otherwise output one or more images, beams of radiation, dynamic stimulus, or other output included in a refractive error examination or other vision test. Further, one or more such inputs may comprise a command or a request for a camera or other image capture device of the vision screening device 104 to obtain one or more images of the patient's eyes during a macular degeneration screening. For example, in any of the examples described herein, the controller 132 may be operable to cause the second display 136 to generate, display, provide, and/or otherwise output one or more Snellen charts, characters, or other images included in a visual acuity examination or other vision test. Likewise, the controller 132 may be operable to cause the second display 136 to generate, display, provide, and/or otherwise output one or more images, beams of radiation, dynamic stimulus, or other output included in a refractive error examination or other vision test. Further, the controller 132 may be operable to cause the image capture device and/or other sensors 140 of the vision screening device 104 to obtain one or more images of the eye during a macular degeneration screening.

The first display 134 may be disposed on a first side of the housing 130 substantially facing the user 102 during operation of the system 100. The second display 136 may be disposed on a second side of the housing 130 opposite the first side of the housing 130. For example, the second display 136 may be disposed opposite the first display 134, and facing the patient 106. The first display 134 may include a graphical user interface configured to display information to the user 102 and/or receive input from the user 102 during any of the tests or procedures described herein. For example, the first display 134 may be configured to receive input from the user 102 regarding the patient 106, such as any of the patient information described herein. Further, the first display 134 may be configured to display information regarding the vision screening device 104 (e.g., a current setting or operating mode of the device, etc.), the distance of the patient 106 from the vision screening device 104, the quality of the environment and/or the focus of the vision screening device 104, the progress of the screening, options for transmitting data from the vision screening device 104 to the vision screening system 110, one or more measurements and/or values generated during the vision screening, one or more images of the eye captured by the image capture device or other sensors 140, etc. The first display 134 may comprise, for example, a liquid crystal display (LCD) or active matrix organic light emitting display (AMOLED). The first display 134 may also be touch-sensitive to receive input from the user 102.

Similar to the first display 134, the second display 136 of the vision screening device 104 may comprise, for example, an LCD or an AMOLED. Additionally or alternatively, the second display 136 may include a light-emitting diode (LED) array including one or more visible LEDs and/or one or more near-infrared LEDs. In some examples, a beam splitter included in the vision screening devise 104 may direct light emitted from such an LED array towards the patient 106. The near-infrared LEDs in the LED array may be configured to emit radiation having a wavelength of approximately 850 nanometers (nm). In some examples, the visible LEDs in the LED array may be configured to emit radiation having a wavelength of less than approximately 630 nm. This allows for a visual stimulus, or graphical representation, to be displayed to the patient 106 without being seen in image/video data captured by the vision screening device 104 (e.g., by an image sensor array, an image capture device, and/or other sensors 140 or components of the vision screening device 104). In some examples, the visible LEDs may be positioned between, and be substantially co-planar with, the near-infrared LEDs in the LED array.

As noted above, although not shown in FIG. 1 it is understood that in some examples the vision screening device 104 may also include computer-readable media and/or other memory operably connected to the controller 132. In such examples, the controller 132 may be operable to record and/or store details (e.g., images of the eye, test results, etc.) of the various vision tests performed by the vision screening device 104 in the memory of the vision screening device 104. In any of the examples described herein, the memory of the vision screening device 104 may store the patient screening components 142 described above, the macular degeneration screening components 144 described above, and/or various other computer-executable instructions executable by one or more processors of the controller 132. When such instructions are executed by one or more processors of the controller 132, such instructions may cause the controller 132 and/or the one or more processors of the controller 132 to perform any of the methods and/or operations described herein.

The one or more controls 138 may comprise a button, a switch, a trigger, a touchscreen, a keyboard, a microphone, an optical sensor, a video sensor, a camera, and/or other control devices configured to receive touch input, audible commands, visual commands (e.g., hand gestures), and/or other input from the user 102. The controls 138 may generate and/or provide corresponding information to the controller 132 based at least in part on receiving such an input from the user 102. In such examples, the controller 132 may be programmed and/or otherwise configured to perform any of the operations described herein based at least in part on the input, and/or based at least in part on the information received from the controls 138. For instance, in any of the examples described herein, the controller 132 may be configured to control operations of the image capture device and/or other sensors 140 of the vision screening device 104 based at least in part on one or more inputs received via the controls 138. In particular, the controller 132 may be configured to cause such an image capture device to obtain one or more images of the patient's eye, either substantially instantaneously or at a predetermined time or cadence, in response to one or more such inputs.

As noted above, the one or more sensors 140 may comprise a digital camera, an image sensing array, and/or other image capture device configured to obtain one or more images of the patient's eyes at relatively close range. For instance, the one or more sensors 140 may comprise a digital retina camera or digital fundus camera having a resolution of approximately 2592 pixels×approximately 1944 pixels (5 MP), and such a camera may be configured to generate one or more encrypted JPEG image files, one or more DICOM® image files, and/or other types of output. Such a camera may be configured to obtain images of the retina, the optic disc, the macula, the posterior pole, and/or other components of the patient's eye, and image files containing such images may be transferred to the vision screening system 110, via the network, 108, for comparison, evaluation, longitudinal tracking, and/or storage. It is understood that in any of the examples described herein, the resolution of such an image capture device may be greater than or less than that described above, and the image capture device or other sensors 140 of the vision screening device 104 may be configured with auto-sensing, auto-focus, auto-alignment, auto-flash adjustment, auto-capture, eye-tracking, and/or other functionality.

The one or more sensors 140 may also comprise one or more light sensors configured to detect the ambient light intensity around the vision screening device 104. For example, above certain brightness thresholds, the pupils of the patient 106 may constrict to the point where some of the vision screening procedures described herein are unreliable or impossible. In this instance, the controller 132, in combination with the one or more light sensors, may determine that the ambient light is too bright and at least one of the first display 134 or the second display 136 may provide instructions to at least one of the user 102 or the patient 106 requesting the use of a light shield, requesting that the user 102 and the patient 106 move to an environment with less ambient light, or requesting an adjustment to the current screening environment.

Additionally or alternatively, the one or more sensors 140 may comprise one or more proximity sensors configured to determine a distance between the patient 106 and the vision screening device 104. In such examples, the sensor 140 may be configured to determine a distance of the patient 106 from the vision screening device 104. In some examples, the sensor 140 may include an infrared transceiver unit, an ultrasonic transceiver unit, or another distance measuring component known in the art.

Figure 2:
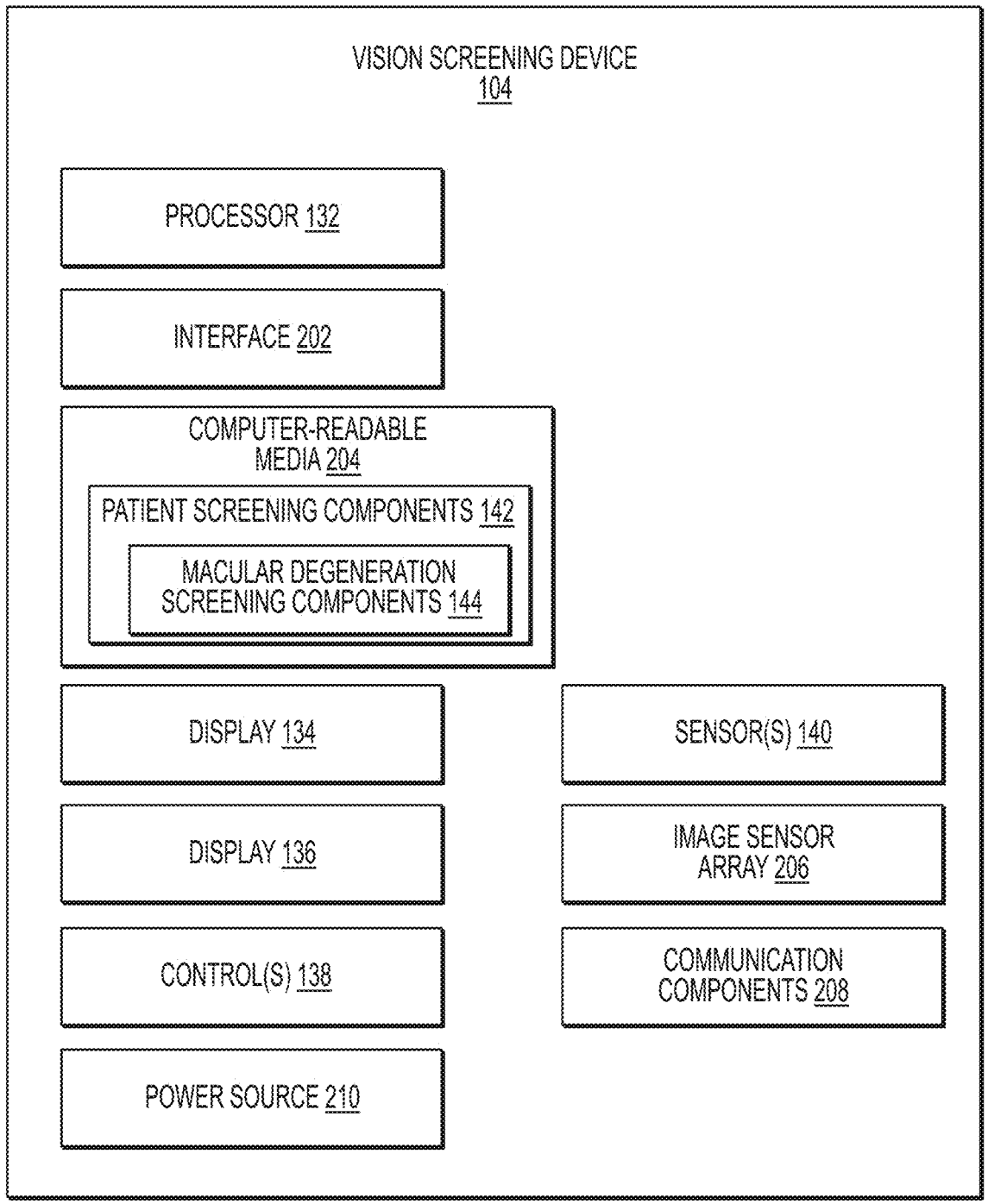
FIG. 2 illustrates another example system of the present disclosure.

FIG. 2 provides a schematic illustration of an example vision screening device 104 of the present disclosure. It is understood that any of the components described above with respect to the vision screening device 104 shown in FIG. 1 may be included in the example vision screening device 104 shown schematically in FIG. 2 regardless of whether such components are expressly illustrated in FIG. 2. Additionally, like components between the vision screening devices 104 shown in FIG. 1 and FIG. 2 are illustrated in FIG. 2 using like item numerals. For example, as shown in FIG. 2, the vision screening device 104 may include one or more processors 132 and/or other controller components. In some examples, the processor 132 shown schematically in FIG. 2 may comprise one or more of the controllers 132 described above with respect to FIG. 1, or vice versa. The vision screening device 104 may also include a first display 134, a second display 136, and one or more controls 138. The vision screening device 104 shown in FIG. 2 may also include one or more sensors 140, and in some examples, one or more of the sensors 140 may include a digital retina camera and/or any of the other image capture devices described above with respect to FIG. 1. Moreover, as will be described in greater detail below, an example vision screening device 104 may include an interface 202, as well as computer-readable media 204 containing the patient screening components 142 and/or the macular degeneration screening components 144 described above. An example vision screening device 104 may also include an image sensor array 206, one or more communication components 208, and/or a power source 210.

In the example shown in FIG. 2, the processor 132 of the vision screening device 104 may comprise one or more controllers, processors, and/or other hardware and/or software components configured to operably control the first display 134, the second display 136, the one or more sensors 140, the image sensor array 206, the communication components 208, and/or other components of the vision screening device 104. For instance, the processor 132 shown in FIG. 2 may include a single processing unit (e.g., a single processor) or a number of processing units (e.g., multiple processors), and can include single or multiple computing units or multiple processing cores. The processor 132 shown in FIG. 2 can be implemented as one or more microprocessors, microcomputers, microcontrollers, digital signal processors, central processing units, state machines, logic circuitries, and/or any devices that manipulate signals based on operational instructions. For example, processor 132 shown in FIG. 2 can be one or more hardware processors and/or logic circuits of any suitable type specifically programmed or configured to execute the algorithms, operations, and methods described herein. The processor 132 shown in FIG. 2 can be configured to fetch and execute computer-readable instructions stored in the computer-readable media 204, which can program the processor 132 to perform the functions described herein. Additionally or alternatively, the processor 132 shown in FIG. 2 can be configured to fetch and execute computer-readable instructions stored in computer-readable media 116 of the vision screening system 110 (FIG. 1).

In any of the examples described herein, the processor 132 shown in FIG. 2 may be configured to receive various information, signals, and/or other inputs from one or more of the controls 138, the sensors 140, the display 134, the display 136, the image sensor array 206, and/or other components of the vision screening device 104. In some examples, the controls 138 may receive such inputs from the user 102, and one or more such inputs may comprise any of the inputs described above associated with one or more macular degeneration screening procedures.

The interface(s) 202 of the vision screening device 104 shown in FIG. 2 may enable wired and/or wireless communications between the vision screening device 104 and one or more components of the vision screening system 110 (FIG. 1), as well as with one or more other remote systems and/or other networked devices. For instance, the interface 202 may include a personal area network component to enable communications over one or more short-range wireless communication channels. Furthermore, the interface 202 may include a wide area network component to enable communication over a wide area network. In any of the examples described herein, the interface 202 may enable communication between the vision screening device 104 and the vision screening system 110 via the network 108 (FIG. 1).

In some respects, the computer-readable media 204 shown in FIG. 2 may be similar to the computer-readable media 116 described above with respect to the vision screening system 110 (FIG. 1). For example, the computer-readable media 204 may include volatile and nonvolatile memory and/or removable and non-removable media implemented in any type of technology for storage of information, such as computer-readable instructions, data structures, program modules, or other data. Such computer-readable media 204 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. The computer-readable media 204 can be a type of computer-readable storage media and/or can be a tangible non-transitory media to the extent that when mentioned, non-transitory computer-readable media exclude media such as energy, carrier signals, electromagnetic waves, and signals per se.

The computer-readable media 204 can be used to store any number of functional components that are executable by the processor(s) 132. In many implementations, these functional components comprise instructions or programs that are executable by the processor(s) 132 and that, when executed, specifically configure the one or more processor(s) 132 to perform the actions described herein and associated with one or more vision screening tests.

With continued reference to FIG. 2, the computer-readable media 204 may include any number of functional components that are executable by the processor(s) 132. In many implementations, these components comprise instructions or programs that are executable by the processor(s) 132 and that, when executed, specifically configure the one or more processors 132 to perform the actions attributed to the vision screening device 104. For example, the patient screening components 142 may be configured to receive, access, store, and/or analyze various data associated with the patient 106 in order to determine patient data for use by the vision screening device 104. For instance, the patient screening components 142 may be configured to receive patient data entered by the user 102 and indicating the date of birth, ethnicity, gender, name, eye color, address, and/or other characteristics of the patient 106 (e.g., patient provided or determined otherwise), as well as a desired vision test to be performed. In examples, the patient screening components 142 may also be configured to receive/access patient data from a database (e.g., the database 120) associated with the vision screening system 110. Still further, in examples, the patient screening components 142 may be configured to receive/access image/video data from the image/video sensor array 206 of the vision screening device 104 and/or any other information from the one or more image capture devices or other sensors 140. The patient screening components 142 may be configured to analyze any such information to determine certain characteristics associated with the patient 106. For example, the macular degeneration screening components 144 described herein may be configured to process images and/or other information received from the image/video sensor array 206 and/or from the one or more image capture devices or other sensors 140 in order to identify the presence of drusen or other indicators of macular degeneration.

For example, the macular degeneration screening components 144 and/or other patient screening components 142 stored in the computer-readable media 204 may include, among other things, a graphical representation data component, a measurement data component, a threshold data component, a notification component, a sensor data component, a range finder data component, a microphone data component, a light source control component, a machine learning component, and/or any other functional component associated with the operation of the vision screening device 104.

For instance, in some examples the patient screening components 142 stored in the computer-readable media 204 may include a graphical representation data component. The graphical representation data component may be configured to determine and/or generate one or more graphical representations for display to the user 102 and/or to the patient 106 during a vision test. For example, the graphical representation data component may be configured to receive and/or access patient data from the patient screening component 206 to determine a characteristic and/or testing category associated with the patient 106 (e.g., toddler, senior, near-sighted, etc.). Utilizing this information, the graphical representation data component may determine a type of graphical representation to generate for display to the patient 106. For example, if the patient data indicates that the patient 106 is being screened for dynamic pupil tracking, the vision screening device 104 may generate a moving image for display to the patient 106 in order to track how the pupil movement of the patient 106 during the screening.

In some examples, the macular degeneration screening components 144 and/or other patient screening components 142 stored in the computer-readable media 204 may also include a measurement data component. For example, the measurement data component may be configured to receive/access image/video data from the image/video sensor array 206 of the vision screening device 104. The measurement data component may also be configured to receive/access images or other sensor data received from any of the image capture devices and/or other sensors 140 described herein. The measurement data component may further be configured to analyze and/or otherwise process such received images or sensor data to determine one or more characteristics of the patient's eye during a macular degeneration screening. For example, the measurement data component may be configured to process the images or other sensor data to identify the optic disc as illustrated in an image, to determine a radius of a circle or other geometric shape approximating the optic disc, to identify a region of interest associated with the macula, to perform a segmentation and/or thresholding process on the image to assist in identifying the center of the macula, to perform further segmentation and/or other thresholding processes on the image to identify drusen in the eye, and to assist in generating an augmented image of the eye. In any of the examples described herein, the measurement data component may comprise and/or may utilize image processing software and/or object identification software to assist in performing one or more of the operations described herein.

In examples, the macular degeneration screening components 144 and/or other patient screening components 142 stored in the computer-readable media 204 may also include a threshold data component. The threshold data component may be configured to receive, access, and/or analyze threshold data associated with images obtained by the image capture device or other sensors 140. For example, the threshold data component may be configured to access or receive data (e.g., stored in the computer-readable media 204) indicating a range of values or other thresholds associated with brightness, darkness, image contrast, distance, dimensions of the optic disc, the location and/or size of a region of interest associated with the macula, etc. Such thresholds may be used to assist in the segmentation, thresholding, and/or other image processing operations performed by during a macular degeneration screening. For example, such thresholds may be used to increase the contrast, resolution, sensitivity, and/or characteristics of the obtained images, and may thus assist with identifying the optic disc, the macula, the fovea, and/or drusen.

Alternatively, or in addition, the threshold data component may be configured to utilize one or more machine learning techniques to determine a range of values or other thresholds associated with brightness, darkness, image contrast, distance, dimensions of the optic disc, the location and/or size of a region of interest associated with the macula, and/or other parameters associated with image processing during a macular degeneration screening. For example, the threshold data component may be configured to utilize one or more algorithms and/or trained machine learning models to determine a range of values or other thresholds associated with the above parameters. For example, the threshold data component may execute one or more algorithms (e.g., decision trees, artificial neural networks, association rule learning, or any other machine learning algorithm) to determine a range of values or other thresholds based on historical macular degeneration screening data. In response, the threshold data component may be configured to utilize the trained models to determine one or more values or thresholds for use by the vision screening device 104.

In examples, the macular degeneration screening components 144 and/or other patient screening components 142 stored in the computer-readable media 204 may also include a notification component. For example, the notification component may be configured to receive and/or access the results of the various vision tests from the measurement data component, and provide an indication of the results to the user 102 conducting the vision test. For instance, the notification component may be configured to output such results via at least one of the first display 134 and/or the second display 136. The notification component may also be configured to provide such results to the vision screening system 110 via the network 108.

In further examples, the computer-readable media 204 may include a microphone component. The microphone component may be configured to receive responses spoken by patient 106 and generate audio data associated with the responses. For example, the patient 106 may provide auditory responses as part of a macular degeneration screening and/or other vision tests described herein. The microphone component may be configured to receive the patient's responses, to generate audio data associated the responses, and/or provide the audio data to the processor 132 shown in FIG. 2. In combination with voice recognition software, the microphone component and/or other functional components of the computer-readable media 204 may decode the responses to generate audio data, and may use the audio data in the various vision tests described herein.

With continued reference to FIG. 5, the image/video sensor array 206 of the vision screening device 104 may be configured to receive and/or access light, image, and/or video data associated with a patient 106 being evaluated during a vision test. In particular, the image/video sensor array 206 may be configured to generate and/or capture image and/or video data during a vision test such as a refractive error test, a visual acuity test, a macular degeneration screening, etc. For example, as described herein, image data and/or video data may be generated by the image/video sensor array 206 during a vision screening to determine initial patient data, one or more measurements associated with the body and eyes of the patient 106, and the like. In some examples, the image/video data may be transmitted, via the interface(s) 202, to the vision screening system 110 for processing and analysis. In any of the examples described herein, the image/video sensor array 206 may be used in combination with and/or in place of the image capture device and/or other sensors 140 to obtain one or more images of the patient's eyes.

In some examples, the image/video sensor array 206 includes, for example, a complementary metal-oxide semiconductor (CMOS) sensor array, also known as an active pixel sensor (APS), or a charge connected device (CCD) sensor. In some examples, a lens is supported by the vision screening device 104 and positioned in front of the image/video sensor array 206. In still further examples, the image/video sensor array 206 has a plurality of rows of pixels and a plurality of columns of pixels. For example, the image/video sensor array 206 may include approximately 1280 by 1024 pixels, approximately 640 by 480 pixels, approximately 1240 by 1130 pixels, approximately 2048 by 1536 pixels, and/or approximately 2560 by 1920 pixels. The image/video sensor array component 210 may be capable of capturing approximately 25 frames per second (fps), approximately 30 fps, approximately 35 fps, approximately 40 fps, approximately 50 fps, approximately 75 fps, approximately 100 fps, approximately 124 fps, approximately 200 fps, approximately 225 fps, and/or approximately 250 fps. Note that the above pixel values and frames per second are exemplary, and other values may be greater or less than the examples described herein.

In examples, the image/video sensor array 206 may include photodiodes having a light-receiving surface and have substantially uniform length and width. During exposure, the photodiodes convert the incident light to a charge. The image/video sensor array 206 may be operated as a global shutter. For example, substantially all of the photodiodes may be exposed simultaneously and for substantially identical lengths of time. Alternatively, the image/video sensor array 206 may be used with a rolling shutter mechanism, in which exposures move as a wave from one side of an image to the other. Other mechanisms are possible to operate the image/video sensor array 206 in yet other examples. The image/video sensor array 206 may also be configured to capture digital images. The digital images can be captured in various formats, such as JPEG, BITMAP, TIFF, etc. As noted above, in some examples the image/video sensor array 206 may be used in combination with and/or in place of the image capture device and/or other sensors 140 to obtain one or more images of the patient's eyes. For instance, in some examples the image/video sensor array 206 may comprise a component of an image capture device and/or other sensor 140 included in the vision screening device 104.

The communication components 208 of the example vision screening device 104 shown in FIG. 2 may be configured to connect to external databases (e.g., the database 120) to receive, access, and/or send image files or other information using wireless connections. Wireless connections can include cellular network connections and connections made using protocols such as 802.11a, b, g, and/or ac. In other examples, a wireless connection can be accomplished directly between the vision screening device 104 and an external display using one or more wired or wireless protocols, such as Bluetooth, Wi-Fi Direct, radio-frequency identification (RFID), or Zigbee. Other configurations are possible. The communication of data to an external database can enable report printing or further assessment of the patient's visual test data. For example, data collected and corresponding test results may be wirelessly transmitted and stored in a remote database accessible by authorized medical professionals.

Further, it is understood that the power source 210 may comprise any removable, rechargeable, and/or other power source known in the art and configured to store electrical power. The power source 210 may comprise one or more rechargeable batteries configured to selectively provide electrical current to the one or more components of the vision screening device 104 during use. For instance, the power source 210 may comprise one or more sealed lead acid batteries, lithium ion batteries, nickel cadmium batteries, nickel-metal hydride batteries, or other types of batteries configured to provide sufficient power to the first display 134, the second display 136, the one or more processors 132, the image capture device and/or other sensors 140, the image sensor array 206, and/or other components of the visions screening device 104 during use.

Figure 3:
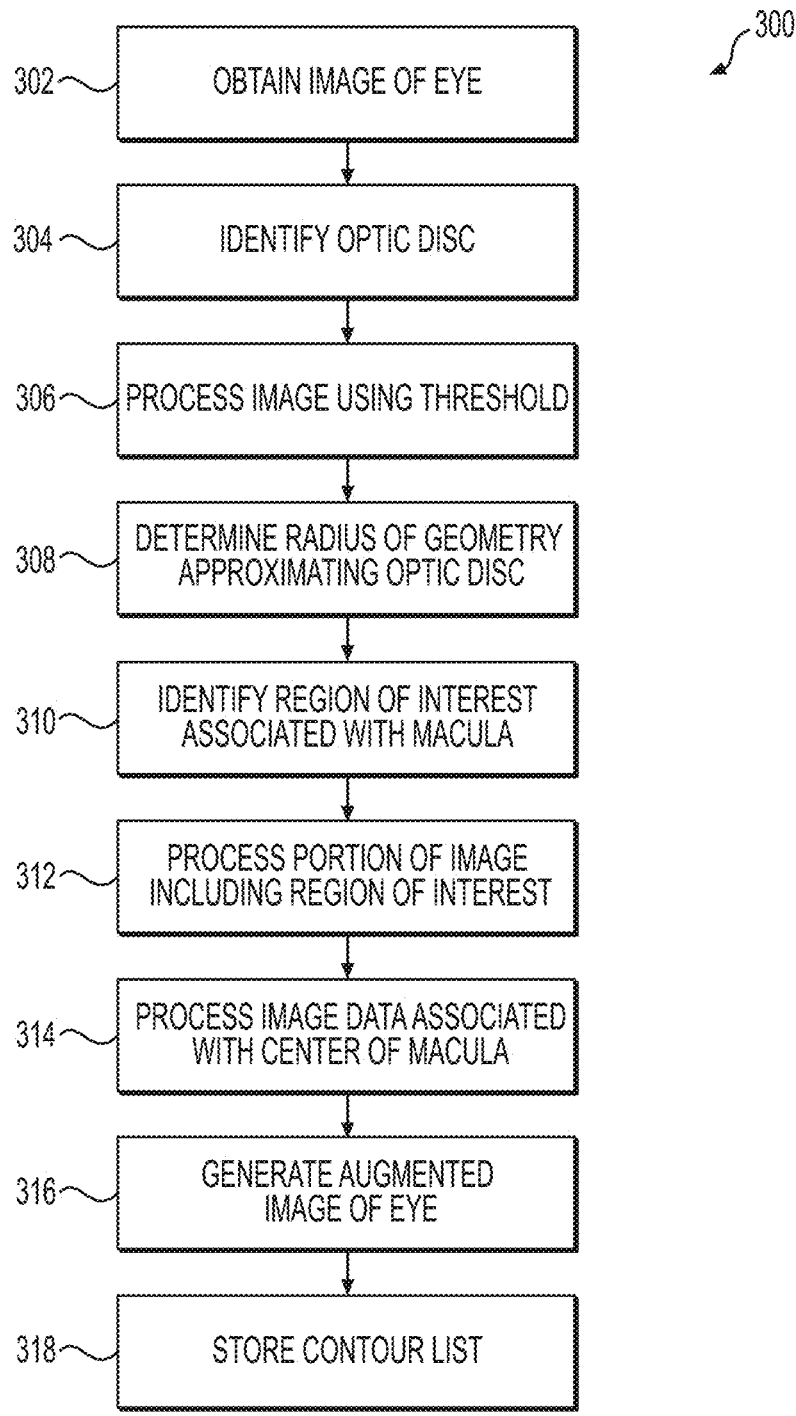
FIG. 3 provides a flow diagram illustrating an example method of the present disclosure.

FIG. 3 provides a flow diagram illustrating an example method 300 for vision testing (e.g., for an example macular degeneration screening), as described herein. The method 300 is illustrated as collections of blocks in a logical flow graph, which represents a sequence of operations that can be implemented in hardware, software, or a combination thereof. In the context of software, the blocks represent computer-executable instructions stored on one or more computer-readable storage media that, when executed by processor(s), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the method 300. In some embodiments, one or more blocks of the method 300 can be omitted entirely.

The operations described below with respect to the method 300 can be performed by any of the systems described herein, and/or by various components thereof. Unless otherwise specified, and for ease of description, the method 300 will be described below with reference to the system 100 shown in FIG. 1. In particular, although any of the operations described with respect to the method 300 may be performed by the controller 132 of the vision screening device 104, the one or more processors 114 of the vision screening system 110, and/or other components of the system 100, either alone or in combination, the method 300 will be described below with respect to the system 100 and/or the controller 132 unless otherwise specified.

Figure 4:
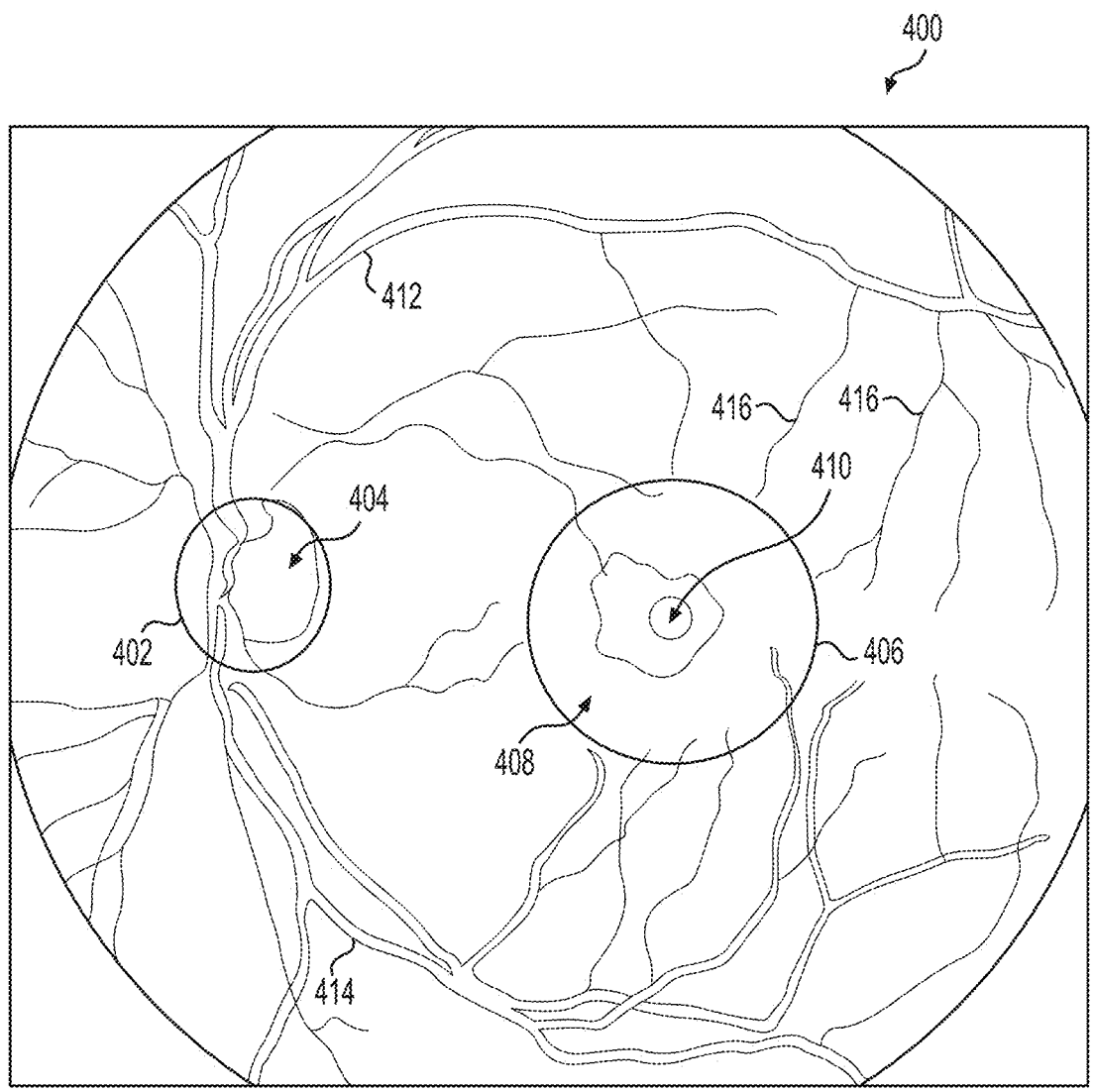
FIG. 4 illustrates an image of a portion of an eye obtained using one or more of the vision screening devices described herein.

At 302, the controller 132 and/or one or more processors associated therewith may control one or more of the image capture devices and/or other sensors 140 described above to capture one or more images of an eye of the patient 106. In such examples, the one or more images captured by an image capture device of the vision screening device 104 may comprise one or more fundus images illustrating the retina, the optic disc, the macula, and/or other components of the eye. Such an example image 400 is illustrated in FIG. 4. In some examples, such an image 400 may comprise a macula-centered image (e.g., an image 400 in which the macula is disposed substantially centrally in the image) and/or other image illustrating at least a portion of the macula. While the image 400 illustrated in FIG. 4 comprise a black-and-white image, it is understood that in any of the examples described herein, the image capture devices, and/or other sensors 140 described herein may capture one or more full-color images. For example, example image capture devices of the present disclosure may capture image data in a variety of colored channels (e.g., a red channel, a green channel, a blue channel, etc.) corresponding to respective wavelengths radiation associated with visible light. In any of the examples described herein, images, and/or image information captured by the various channels of the image capture device may be processed together and/or separately by the controller 132.

As shown in FIG. 4, an example image 400 may illustrate one or more components of the patient's eye. For example, the region 402 of the image 400 may illustrate the optic disc, and the region 406 of the image 400 may illustrate, at least part of the macula 408. In some examples, the image 400 may illustrate the macula 408 and the fovea 410. In various examples, the image 400 may further illustrate the major upper arche 412 the major lower arche 414, and/or other vasculature 416.

Figure 5A:
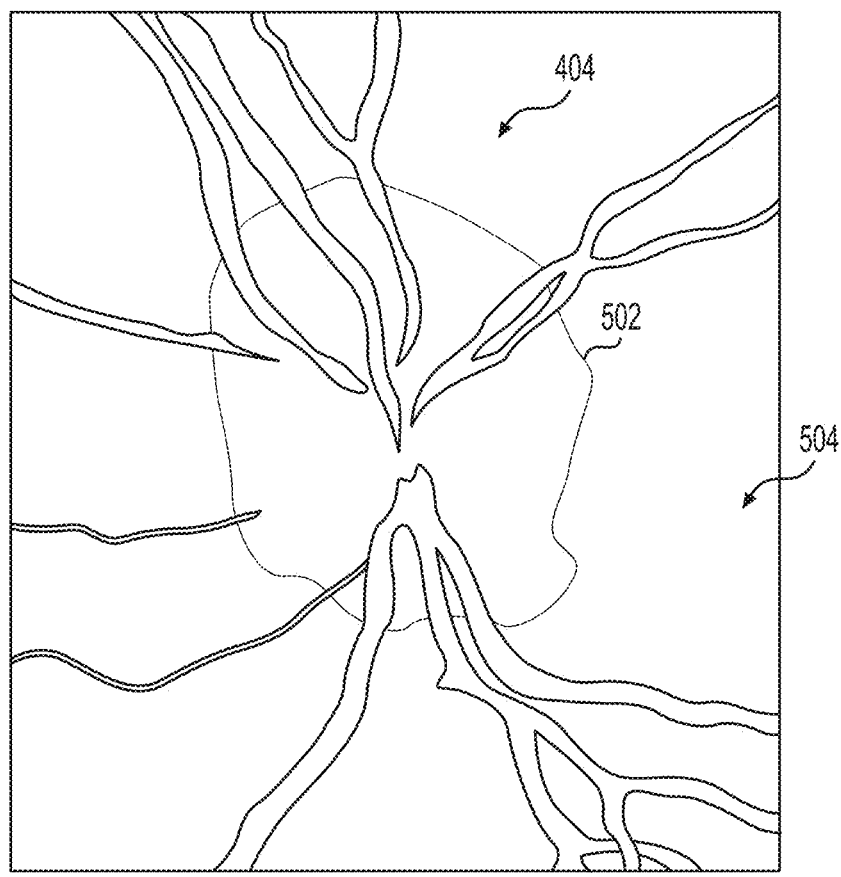
FIG. 5A illustrates an example image of an optic disc.

At 304, the controller 132 and/or one or more processors associated therewith may process at least part of the image 400 to identify the optic disc 404, and/or other components of the eye illustrated in the image 400. For example, one or more image processing components, object identification, components, and/or other macular degeneration screening components 144 employed by the controller 132 may identify the optic disc 404 based at least in part on one or more brightness values associated with individual pixels of the image 400. For example, in fundus images such as the image 400, the optic disc 404 may appear as the brightest object in the image. Accordingly, at 304, the controller 132 may identify a group of pixels having brightness values greater than or equal to a first brightness threshold indicative of the optic disc 404. Such a first brightness threshold (e.g., a first brightness value) may be, for example, 200 on a scale of 0 (black) to 255 (fully white). In other examples, one or more other first brightness thresholds (e.g., brightness values greater than or less than 200) may also be utilized by the controller 132 when identifying the optic disc 404, and it is understood that such thresholds may be selected based on a desired level of sensitivity. In any of the examples described herein, at 304, the controller 132 may identify a pixel or grouping of pixels having the highest relative brightness within the image 400, and may characterize such pixels as representing the optic disc 404 in the image 400. For example, FIG. 5A illustrates a portion of the image 400, including the optic disc 404. For illustrative purposes, the portion of the image 400 shown in FIG. 5A also shows a contour 502 outlining and/or approximating a perimeter of the optic disc 404, as well as a region 504 of the eye surrounding the optic disc 404.

At 306, the controller 132 and/or one or more processors associated therewith may process the portion of the image 400 illustrating the optic disc 404 utilizing one or more thresholds, segmentation techniques, and/or other image processing techniques described herein. For example, at 306 the controller 132 may modify the brightness of the respective pixels included in the portion of the image 400 illustrating the optic disc 404 based at least in part on whether the actual brightness of such pixels is greater than or equal to a second brightness threshold. Such a second brightness threshold (e.g., a second brightness value) may be, for example, 180 on a scale of 0 (black) to 255 (fully white). In other examples, such a second brightness threshold may comprise a brightness value equal to approximately 90% of the highest brightness value associated with the pixels included in the portion of the image 400 being processed. In still other examples, one or more other second brightness thresholds (e.g., brightness values greater than or less than those noted above) may also be utilized by the controller 132 at 306. In some examples, the second brightness threshold may comprise a dynamic threshold based on the relative brightness of the region of the eye illustrated in the portion of the image 400 being processed.

Figure 5B:
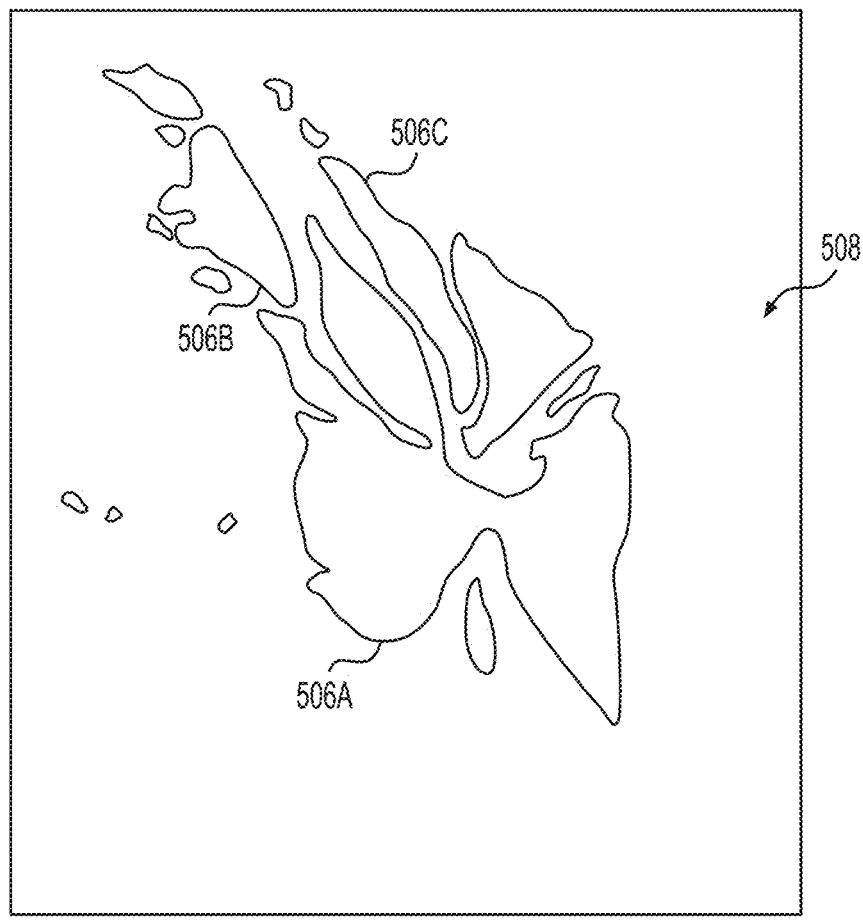
FIG. 5B illustrates a processed image of the optic disc illustrated in FIG. 5A.

In any of the examples described herein, if the actual brightness of a pixel included in the portion of the image 400 being processed is greater than or equal to the second brightness threshold, at 306 the controller 132 may change the brightness value of that pixel to 255 (fully white). Moreover, if the actual brightness of a pixel included in the portion of the image 400 being processed is less than the second brightness threshold, at 306 the controller 132 may change the brightness of that pixel to 0 (fully black). FIG. 5B illustrates an example resulting image generated by the controller 132 at 306. Such an example image may include one or more contours 506A, 506B, 506C corresponding to the pixels modified at 306 to have a brightness value of 255. In such an example image the contours 506A, 506B, 506C may appear as fully white blobs, shapes, or other objects. Taken together, such contours 506A, 506B, 506C may be indicative of the configuration (e.g., the shape, size, perimeter, location, etc.) of the optic disc 404. Such an example image may also include one or more regions 508 surrounding the various contours 506A, 506B, 506C. The regions 508 may correspond to the pixels modified at 306 to have a brightness value of 0. In such an example image, the regions 508 may appear as a fully black background, or as fully black blobs, shapes, or other objects.

Figure 5C:
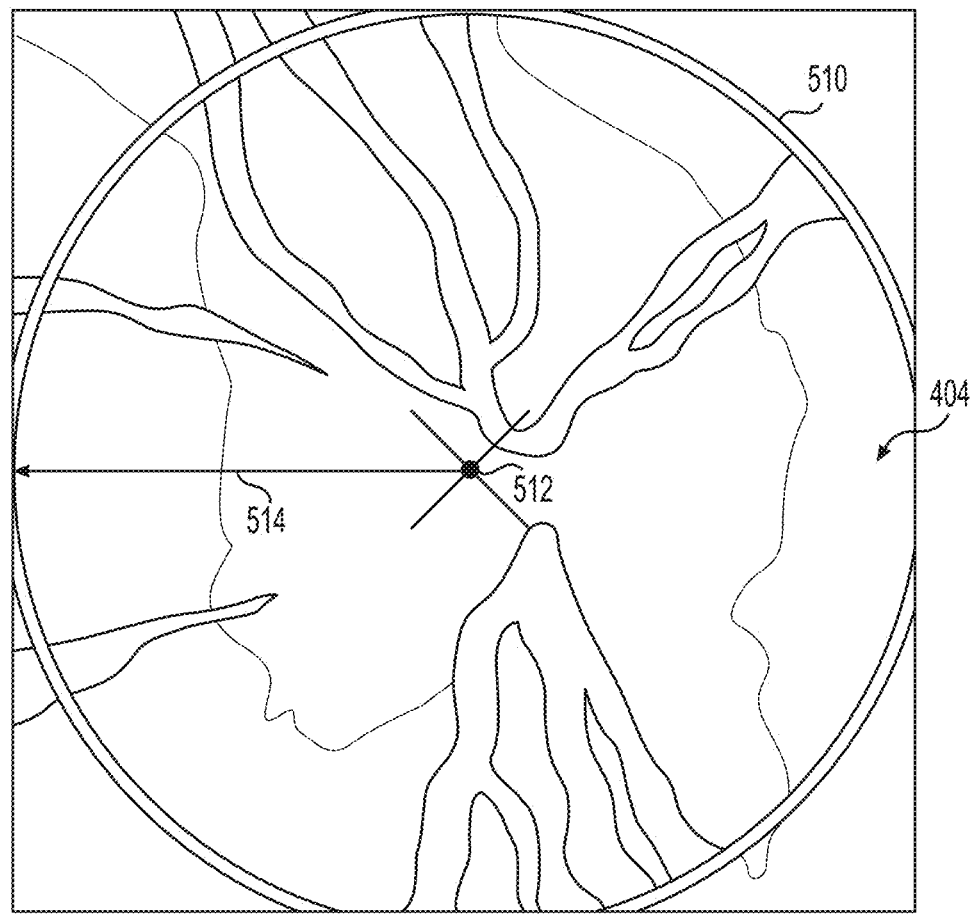
FIG. 5C illustrates another example image of the optic disc shown in FIG. 5A.

At 306, the controller 132 and/or one or more processors associated therewith may also generate a geometric shape fitted to one or more of the contours 506A, 506B, 506C illustrated in FIG. 5B. For instance, in some examples the controller 132 may generate a circle, a square, a rectangle, a triangle, and/or other shape that is dimensioned to substantially surround the largest of the one or more contours 506A, 506B, 506C illustrated in FIG. 5B. In other examples, the controller 132 may generate a circle, a square, a rectangle, a triangle, and/or other shape that is dimensioned to substantially surround all of the contours 506A, 506B, 506C illustrated in FIG. 5B. Such an example geometric shape 510 (e.g., a circle) is illustrated in FIG. 5C. In some examples, the geometric shape 510 may be positioned such that a centerpoint 512 of the geometric shape 510 overlays a centroid of the largest of the one or more contours 506A, 506B, 506C. In other examples, on the other hand, the geometric shape 510 may be positioned such that the centerpoint 512 overlays a cumulative centroid of all of the contours 506A, 506B, 506C illustrated in FIG. 5B. In the example shown in FIG. 5C, the geometric shape 510 (e.g., a circle) may include a radius 514 extending from the centerpoint 512 to a perimeter (e.g., a circumference) of the geometric shape 510.

At 308, the controller 132 and/or one or more processors associated therewith may determine the radius 514 of the geometric shape 510 approximating the optic disc 404. For example, as noted above, the contours 506A, 506B, 506C may appear as fully white blobs, shapes, or other objects in FIG. 5B, and when taken together, such contours 506A, 506B, 506C may be indicative of the configuration (e.g., the shape, size, perimeter, location, etc.) of the optic disc 404. Accordingly, at 308, the controller 132 may determine the length of the radius 514 (e.g., in pixels, in standard dimensional units, etc.) utilizing one or more image processing techniques. In some examples, the controller 132 may utilize the length of the radius 514 determined at 308 as an approximation of, for example, the radius of the optic disc 404.

At 310, the controller 132 and/or one or more processors associated therewith may identify a region of interest associated with the macula 408 based at least in part on the radius 514 determined at 308. In further examples, the controller 132 may identify the region of interest based at least in part on a diameter, a circumference, an area, a perimeter, one or more angles, and/or any other characteristics of the geometric shape described above with respect to 306, 308. For example, as illustrated in the example fundus image shown in FIG. 6, at 310 the controller 132 may identify a region of interest 602 that is defined by a geometric shape 604. It is understood that the image shown in FIG. 6 may comprise a portion of the image 400 shown in FIG. 4. Such an example geometric shape 604 may comprise a square, a circle, a rectangle, a triangle, and/or other shape that is dimensioned to substantially surround the macula 408 in the illustrated image. In the example image shown in FIG. 6, the geometric shape 604 comprises a square having a centerpoint 606 that is disposed at a desired distance 608 from the geometric shape 510. In some examples, the centerpoint 606 of the geometric shape 604 may be disposed at a distance 608 from the centerpoint 512 of the geometric shape 510, and the distance 608 may be, for example, a function of the radius 514. For instance, in some examples the distance 608 may be greater than or equal to approximately 2.0 times the length of the radius 514. For instance, in an example in which the length of the radius 514 equals 100 pixels, the distance 608 may be greater than or equal to approximately 200 pixels. In such an example, the centerpoint 606 of the geometric shape 604 may be disposed at least approximately 200 pixels away from the centerpoint 512 of the geometric shape 510. In other examples, the distance 608 may be less than approximately 2.0 times the length of the radius 514. In further examples, the distance 608 may be greater than or equal to approximately 3.0 times the radius 514, greater than or equal to approximately 4.0 times the radius 514, greater than or equal to approximately 5.0 times the radius 514, and/or greater than or equal to any other function of the radius 514.

Figure 6:
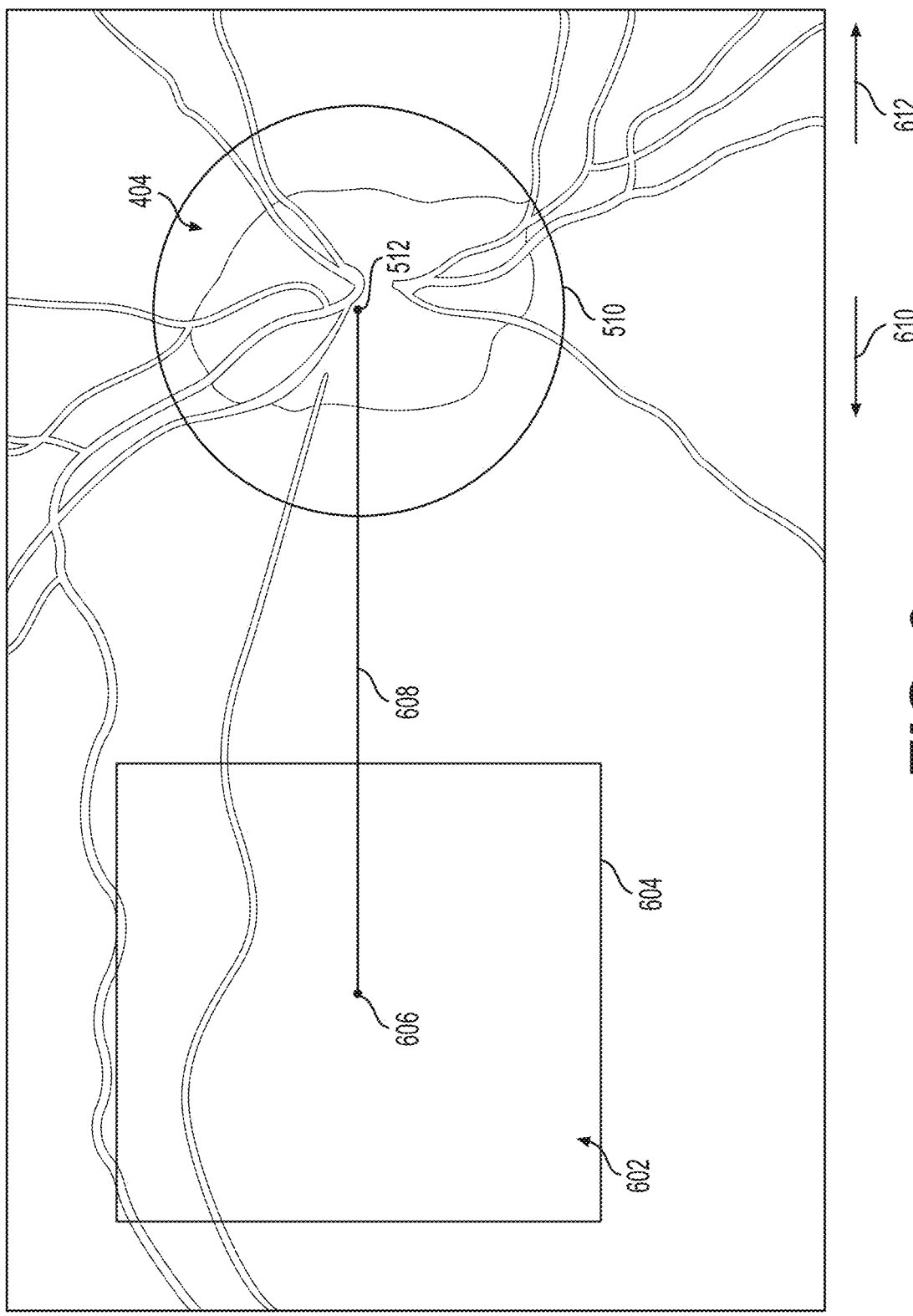
FIG. 6 illustrates an example image of an optic disc and a region of interest.

As shown in FIG. 6, in an example image in which the optic disc 404 and/or the geometric shape 510 is disposed on the right-hand side of the image, the geometric shape 604 may be disposed substantially horizontally (e.g., laterally) away from the geometric shape 510 in the direction 610. Alternatively, in an example image in which the optic disc 404 and/or the geometric shape 510 is disposed on the left-hand side of the image, the geometric shape 604 may be disposed substantially horizontally (e.g., laterally) away from the geometric shape 510 in the direction 612. Further, the geometric shape 604 may have any size, dimensions, and/or other configurations configured to substantially fully encompass the macula 408 during, further image processing operations of the method 300. For example, in embodiments in which the geometric shape 604 identifying the region of interest 602 comprises a square, each side of the square may have a length equal to approximately 4.0 times the length of the radius 514. For instance, in an example in which the length of the radius 514 equals 100 pixels, the length of each side of the square geometric shape 604 shown in FIG. 6 may be equal to approximately 400 pixels. It is understood that in further examples, the distance 608, the radius 514, the length of each side of the square geometric shape 604, and/or any of the other parameters described herein may have values greater than or less than those described above.

At 312, the controller 132 and/or one or more processors associated therewith may process at least a portion of an image (e.g., a portion of the image shown in FIG. 6) including the region of interest 602 in order to identify the center of the macula 408 (e.g., the fovea 410). For example, at 312, the controller 132 may perform one or more procedures similar to those described above with respect to 306 and utilizing one or more thresholds, segmentation techniques, and/or other image processing techniques. For instance, at 312 the controller 132 may modify the brightness of the respective pixels included in the portion of the image illustrating the region of interest 602 based at least in part on whether the actual brightness of such pixels is greater than or equal to a third brightness threshold. Such a third brightness threshold (e.g., a third brightness value) may be significantly less than the first and second brightness thresholds described above such that most of the pixels within the region of interest 602 are turned black. Such an example third brightness threshold may be, for example, 100 on a scale of 0 (black) to 255 (fully white). In other examples, such a third brightness threshold may comprise a brightness value equal to approximately 10% of the highest brightness value associated with the pixels included in the region of interest 602. In still other examples, one or more other third brightness thresholds (e.g., brightness values greater than or less than those noted above) may also be utilized by the controller 132 at 312.

In any of the examples described herein, if the actual brightness of a pixel included in the portion of the image illustrating the region of interest 602 is greater than or equal to the third brightness threshold, at 312 the controller 132 may change the brightness value of that pixel to 255 (fully white). Moreover, if the actual brightness of a pixel included in the portion of the image illustrating the region of interest 602 is less than the third brightness threshold, at 312 the controller 132 may change the brightness of that pixel to 0 (fully black). An example resulting image generated by the controller 132 at 312 may be similar to the image described above with respect to FIG. 5B, except that the various contours illustrated in such an image may be black instead of white. For instance, such an example image generated by the controller 132 at 312 may include one or more contours corresponding to the pixels modified at 312 to have a brightness value of 0. In such an example image the resulting contours may appear as fully black blobs, shapes, or other objects. Taken together, such contours may be indicative of the configuration (e.g., the shape, size, perimeter, location, etc.) of the macula 408. Such an example image may also include one or more regions surrounding the various contours. Such regions may correspond to the pixels modified at 312 to have a brightness value of 255, and in such an example image, such regions may appear as a fully white background, or as fully white blobs, shapes, or other objects. Further, at 312 the controller 132 may identify the largest fully black contour as defining, for example, the fovea 410. In such examples, at 312 the controller 132 may identify the centroid of the largest black contour, and such a centroid may represent the center of the macula 408 for further image processing steps included in the method 300. For example, directing further image processing operations to areas of the one or more captured image in close proximity to the determined center of the macula 408 can significantly reduce the volume of such image processing and the processing resources required for such image processing. Directing further image processing operations to areas of the one or more captured image in close proximity to the determined center of the macula 408 can also significantly reduce the false positive identification of drusen.

Figure 7A:
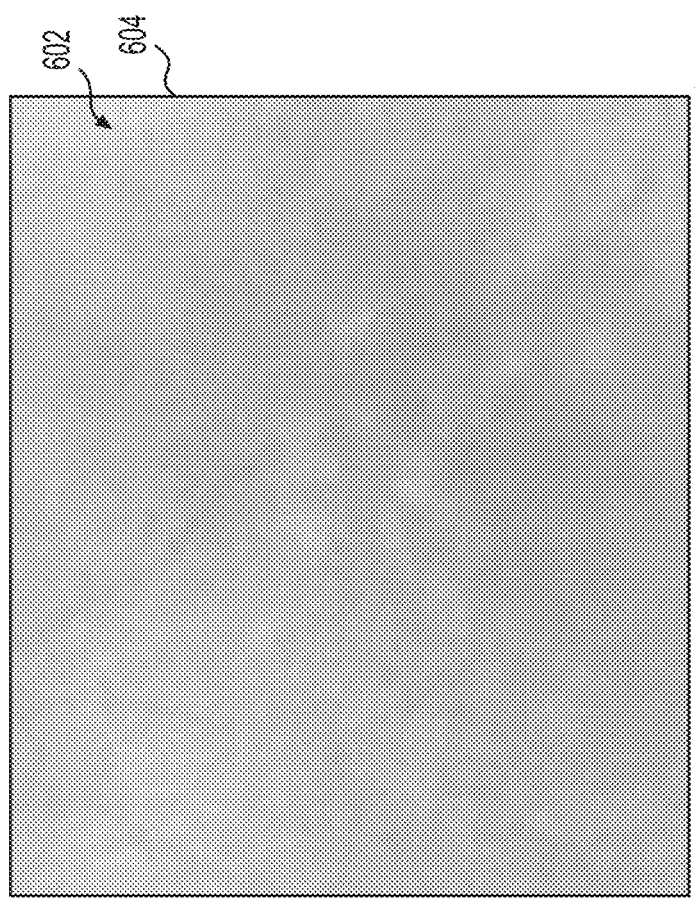
FIG. 7A illustrates an example image of the region of interest shown in FIG. 6.

At 314, the controller 132 and/or one or more processors associated therewith may process one or more images and/or image data associated with the center of the macula identified at 312. For example, at 314 the controller 132 may isolate and/or utilize image data captured by a single channel (e.g., the red channel, the green channel, etc.) of the image capture device and/or other sensors 140. For instance, FIG. 7A illustrates image data captured by the red channel of the image capture device associated with the vision screening device 104. In particular, FIG. 7A illustrates image data captured by the red channel of the image capture device and illustrating the region of interest 602 described above with respect to FIG. 6. In such examples, the centerpoint 608 (FIG. 6) of the geometric shape 604 shown in the image of FIG. 7A may overlay the center of the macula 108 determined at 312.

Figure 7B:
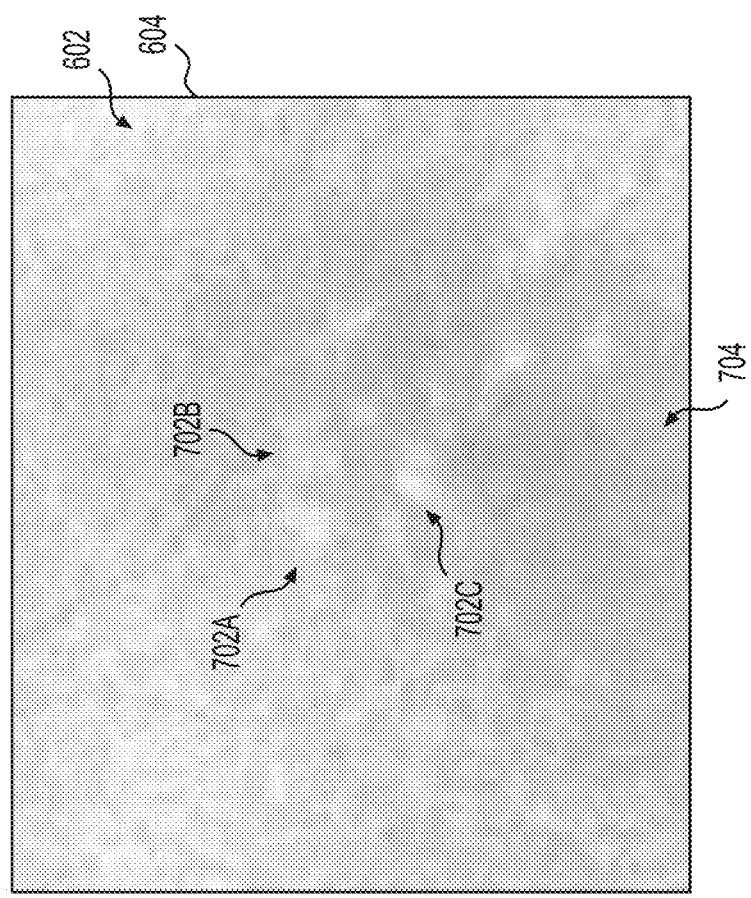
FIG. 7B illustrates another example image of the region of interest.

At 314, the controller 132 may utilize, for example, one or more of the macular degeneration screening components 144 to perform a histogram equalization process on the image shown in FIG. 7A. For example, at 314 the controller 132 may apply a contrast limited adaptive histogram equalization to the image data captured by the red channel of the image capture device. As shown in FIG. 7B, performing such a histogram equalization may yield an image of the region of interest 602 illustrating one or more contours 702A, 702B, 702C outlining and/or approximating perimeters of respective drusen. As can be seen from FIG. 7B, such a histogram equalization process may increase the contrast and/or other visual parameters of the contours 702A, 702B, 702C (relative to the image shown in FIG. 7A and/or relative to a region 704 surrounding the contours 702A, 702B, 702C), and may thus assist in illustrating the edges/perimeters of the contours 702A, 702B, 702C with greater clarity and/or sharpness.

In some examples, at 314 the controller 132 may also utilize one or more of the macular degeneration screening components 144 to perform a dilation process on the image shown in FIG. 7B. As can be seen from the image shown in FIG. 7C, such a dilation process may further increase the contrast and/or other visual parameters of dilated contours 706A, 706B, 706C relative to the region 704 surrounding the dilated contours 706A, 706B, 706C. Thus, such an example dilation process may assist in illustrating the edges/perimeters of the dilated contours 706A, 706B, 706C with even further clarity and sharpness. It is understood that in still further examples, at 314 the controller 132 may also utilize one or more of the macular degeneration screening components 144 to perform a blurring process on the image shown in FIG. 7B. Such a blurring process may assist in reducing the contrast between the contours 702A, 702B, 702C shown in the image of FIG. 7B and the region 704. For instance, such a blurring process (and such a reduction in contrast) may force contours having a brightness value that would have been less than the third brightness threshold described above with respect to FIG. 7B to have a brightness value greater than or equal to the third brightness threshold. As a result, such an example blurring step may increase the sensitivity of the various drusen identification techniques described herein.

With continued reference to FIG. 7C, at 314 the controller 132 may also perform one or more procedures similar to those described above with respect to 306 and utilizing one or more thresholds, segmentation techniques, and/or other image processing techniques. For instance, at 312 the controller 132 may modify the brightness of the respective pixels included in the portion of the image illustrating the region of interest 602 based at least in part on whether the actual brightness of such pixels is greater than or equal to a fourth brightness threshold. Such a fourth brightness threshold (e.g., a fourth brightness value) may be similar to and/or the same as one or more of the first, second, and third brightness thresholds described above. Such an example fourth brightness threshold may be, for example, 150 on a scale of 0 (black) to 255 (fully white). In other examples, such a fourth brightness threshold may comprise a brightness value equal to approximately 50% of the highest brightness value associated with the pixels included in the region of interest 602. In still other examples, one or more other fourth brightness thresholds (e.g., brightness values greater than or less than those noted above) may also be utilized by the controller 132 at 314.

In any of the examples described herein, if the actual brightness of a pixel included in the image of the region of interest 602 shown in FIG. 7C is greater than or equal to the fourth brightness threshold, at 314 the controller 132 may change the brightness value of that pixel to 255 (fully white). Moreover, if the actual brightness of a pixel included in the image of the region of interest 602 shown in FIG. 7C is less than the fourth brightness threshold, at 314 the controller 132 may change the brightness of that pixel to 0 (fully black). An example resulting image generated by the controller 132 at 314 is shown in the binary image 708 of FIG. 7D.

Such an example binary image 708 may illustrate a plurality of contours 710A, 710B, 710C representing one or more configurations and/or characteristics (e.g., the shape, size, area, perimeter, location, opacity, color, etc.) of drusen disposed within the region of interest 602. Such contours 710A, 710B, 710C may comprise components of the binary image 708, and such contours 710A, 710B, 710C may correspond to the pixels modified at 314 to have a brightness value of 255. In such an example image 708, such contours 710A, 710B, 710C may appear as fully white blobs, shapes, or other objects. Such an example binary image 708 may also illustrate one or more regions 712 surrounding the various contours 710A, 710B, 710C and/or other components of the binary image 708. Such regions 712 may correspond to the pixels modified at 314 to have a brightness value of 0. The regions 712 may appear as fully black blobs, shapes, or other objects, and/or may appear as a fully black background.

Figure 7D:
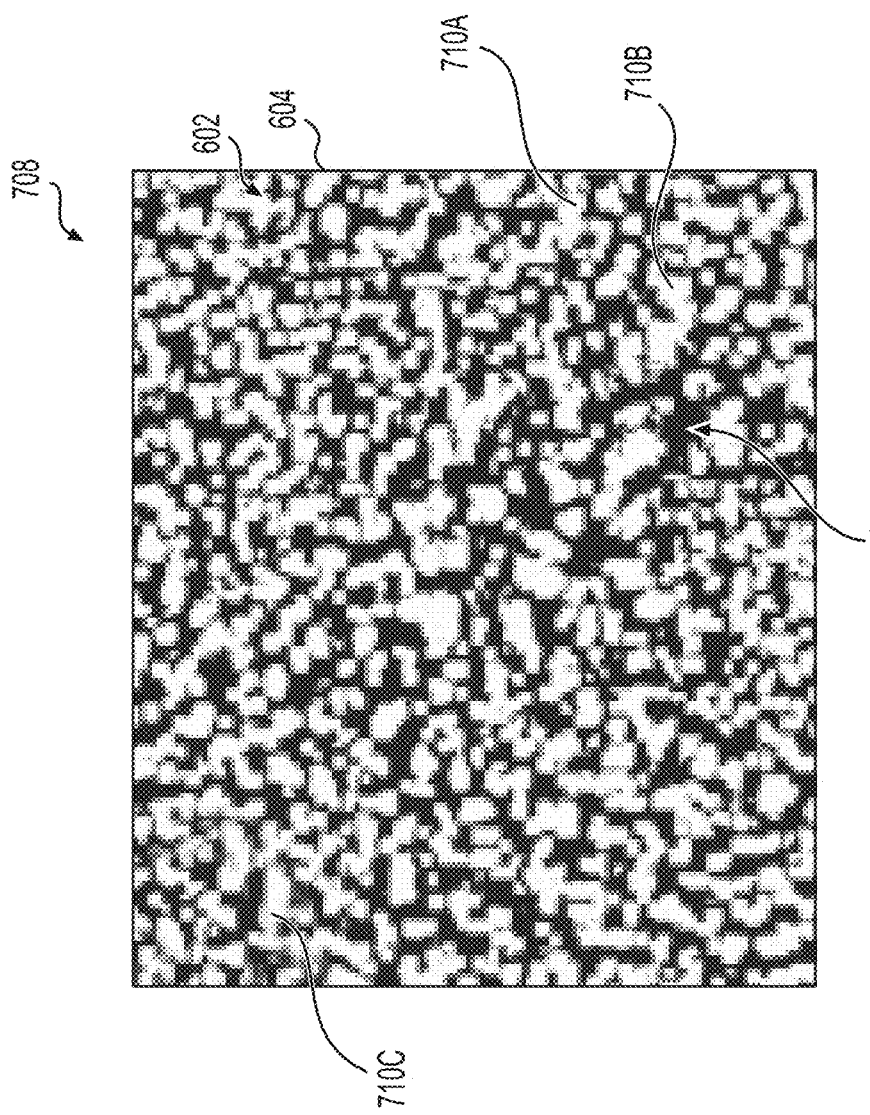
FIG. 7D illustrates still another example image of the region of interest.

Further, at 314 the controller 132 may determine the area (e.g., in pixels, in standard measurement units, etc.) of each of the contours 710A, 710B, 710C and/or other components shown in the image of FIG. 7D. The controller 132 may compare the determined area of each such contour and/or other component to an area threshold (e.g., 100 square pixels), and may identify a subset of the components shown in the image of FIG. 7D having respective areas greater than or equal to the area threshold.

At 316, the controller 132 and/or one or more processors associated therewith may generate one or more augmented images of the eye of the patient 106. For example, at 316 the controller 132 may superimpose outlines and/or other images of the subset of components shown in the image of FIG. 7D having respective areas greater than or equal to the area threshold noted above onto the image 400 obtained at 302. As an example, at 316 the controller 132 may superimpose outlines and/or other images of a subset of the contours 710A, 710B, 710C described above, and having respective areas greater than or equal to the area threshold noted above, onto the image 400 obtained at 302. As a result, the one or more configurations and/or other characteristics (e.g., the shape, size, area, perimeter, location, opacity, color, etc.) of drusen disposed within the region of interest 602 and indicated by the components/contours may be illustrated in an augmented image. In any of the examples described herein, such components of the augmented image may include one or more of the contours described herein (e.g., contours outlining, overlaying, and/or otherwise identifying at least part of a perimeter of drusen located in a region of interest). Additionally or alternatively, such components of the augmented image may include, among other things, one or more arrows, geometric shapes (e.g., circles, squares, etc.), icons, shaded areas, colored areas, blinking areas, text, and/or other visual indicia indicating the configurations and/or other characteristics of drusen identified within the region of interest 602.

Figure 8A:
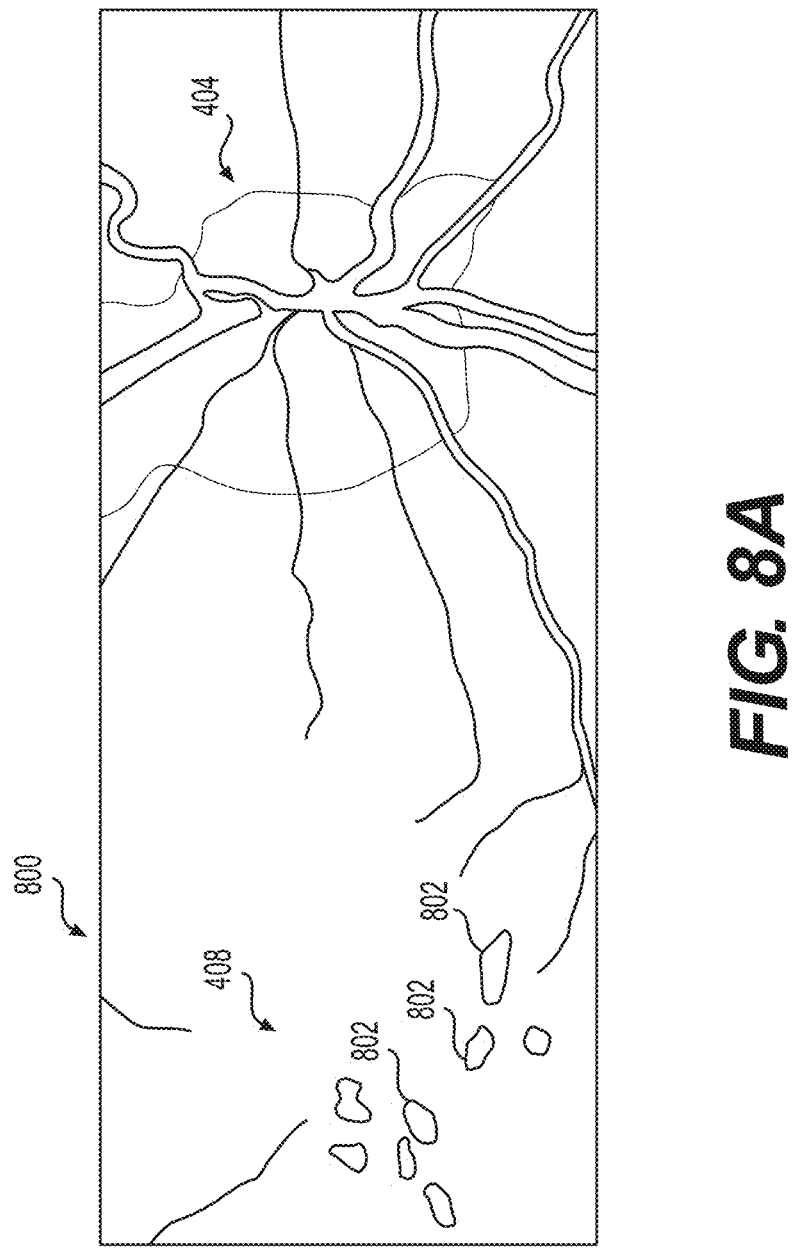
FIG. 8A illustrates an example image of the portion of the eye shown in FIG. 4.
Figure 8B:
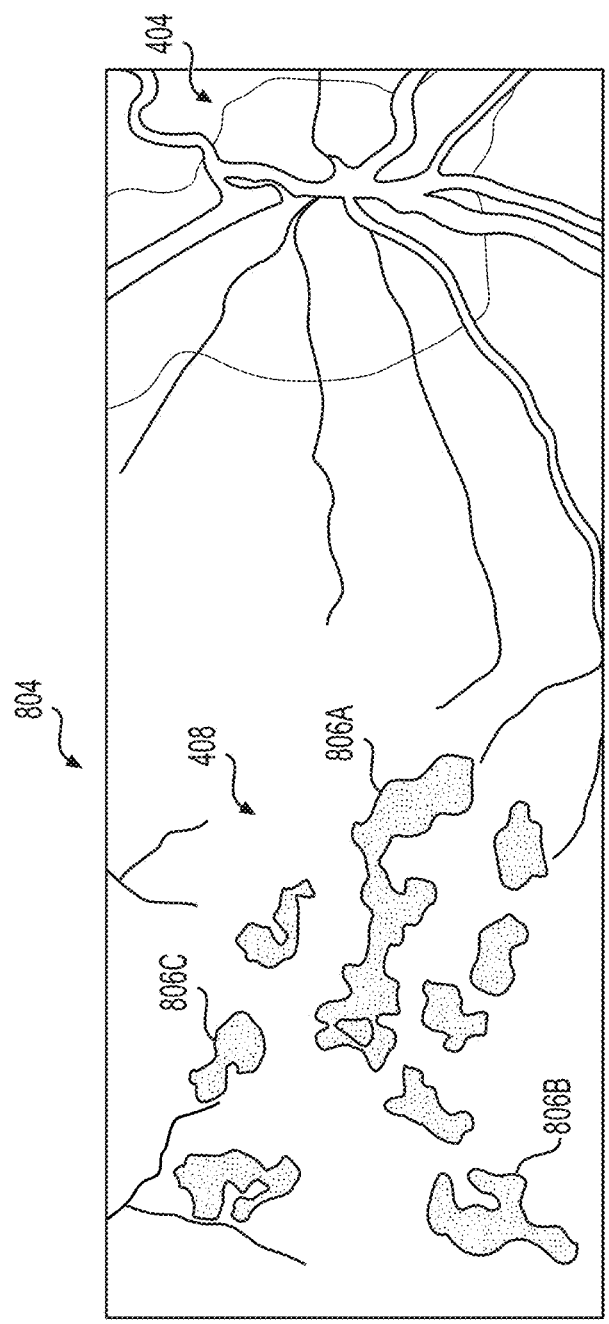
FIG. 8B illustrates an example augmented image of the portion of the eye shown in FIG. 4.

For instance, FIG. 8A illustrates an image 800. The image 800 comprises a portion of the image 400 described above with respect to FIG. 4. As shown in the image 800, one or more objects 802 appearing to be drusen disposed proximate the macula 408 may be at least partially visible in such an image 800. FIG. 8B, on the other hand, illustrates an augmented image 804 generated by the controller 132 at 316. The example augmented image 804 shown in FIG. 8B illustrates components (e.g., contours 806A, 806B, 806C) corresponding to the subset of the contours shown in the image of FIG. 7D having respective areas greater than or equal to the area threshold described above. In such examples, the contours 806A, 806B, 806C and/or other components shown in the augmented image 804 may assist in identifying drusen disposed proximate the macula 408 (e.g., disposed within the region of interest 602 described above) with greater accuracy, and potentially at an earlier stage of macular degeneration.

Figure 9A:
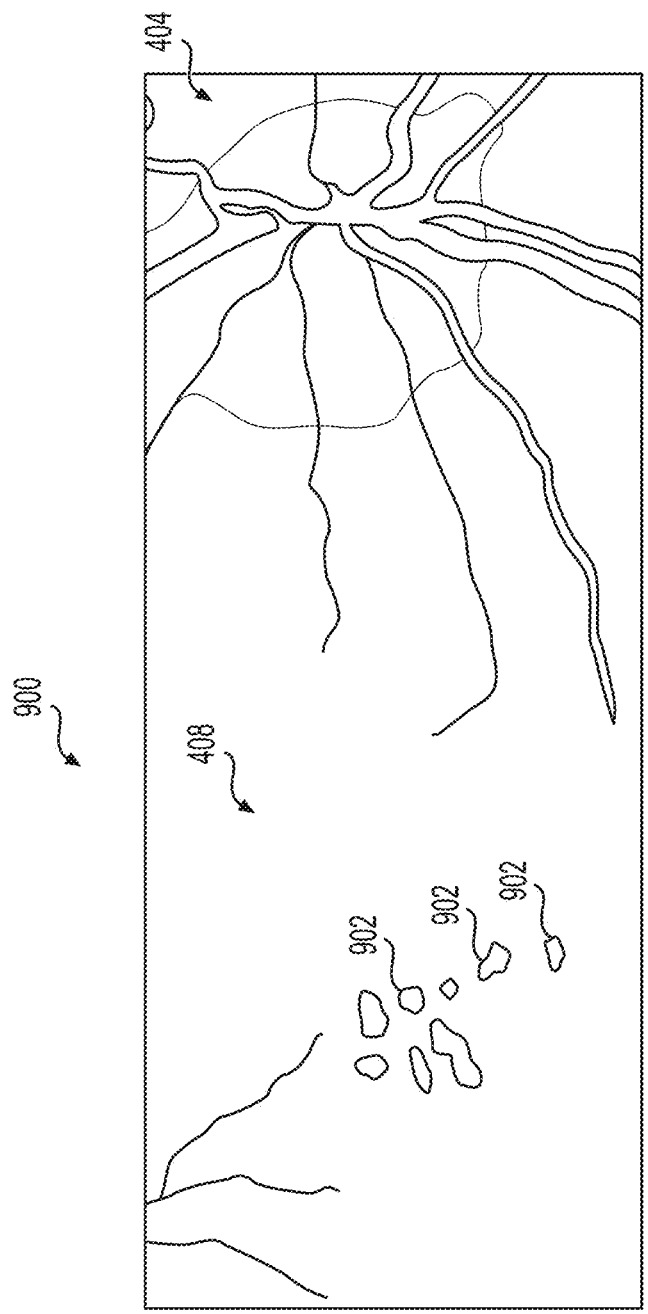
FIG. 9A illustrates another example image of the portion of the eye shown in FIG. 4.
Figure 9B:
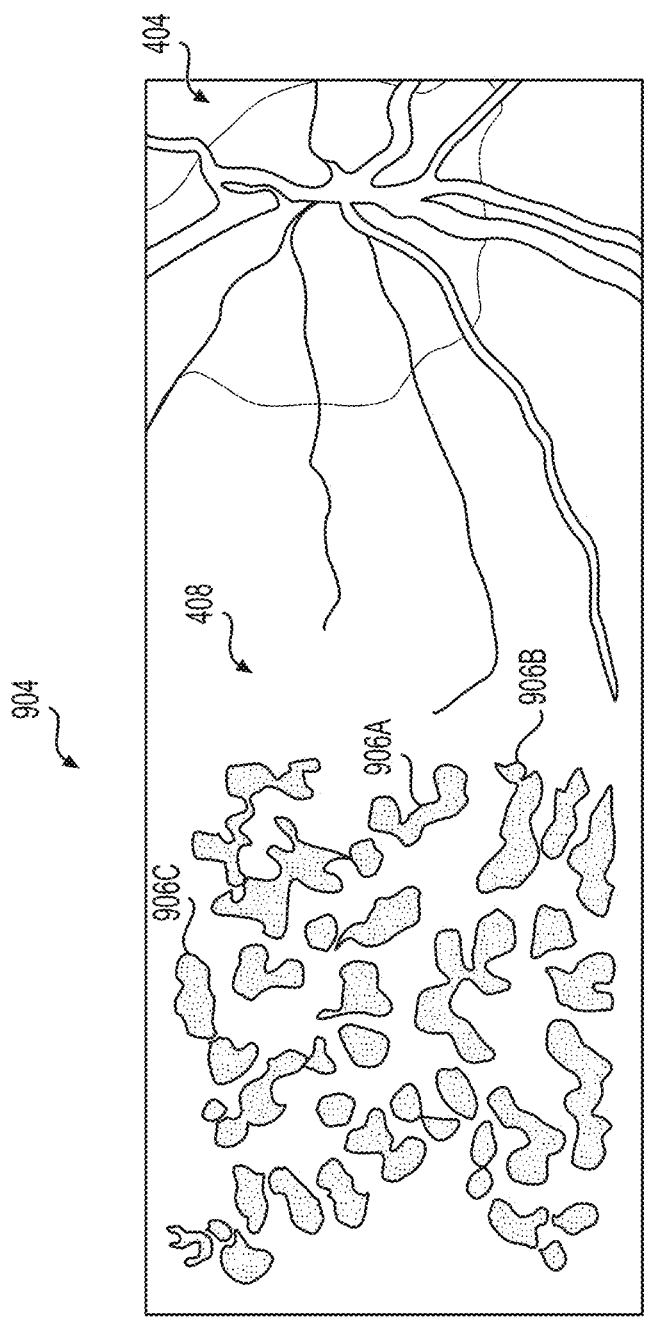
FIG. 9B illustrates another example augmented image of the portion of the eye shown in FIG. 4.

Further, FIG. 9A illustrates another image 900 comprising a portion of the image 400 described above with respect to FIG. 4. As shown in the image 900, one or more objects 902 appearing to be drusen disposed proximate the macula 408 may be at least partially visible from a truncated fundus image obtained using the image capture device and/or other sensors 140 described herein. FIG. 9B, on the other hand, illustrates another example augmented image 904 generated by the controller 132 at 316. The example augmented image 904 shown in FIG. 9B illustrates components (e.g., contours 906A, 906B, 906C) corresponding to the subset of the contours shown in the image of FIG. 7D. As noted above, at 314 the controller 132 may identify such contours as having respective areas greater than or equal to a desired area threshold. In particular, the contours 906A, 906B, 906C and/or other components shown in FIG. 9B correspond to an example subset of relatively large-area contours found at 314 when the optional blurring process was applied to the image shown in FIG. 7B. As can be seen in FIG. 9B, and as noted above, such a blurring process may increase sensitivity when identifying drusen and, as a result, the controller 132 may include a larger number of contours 906A, 906B, 906C in the augmented image 904 shown in FIG. 9B relative to the augmented image 804 shown in FIG. 8B.

Figure 10:
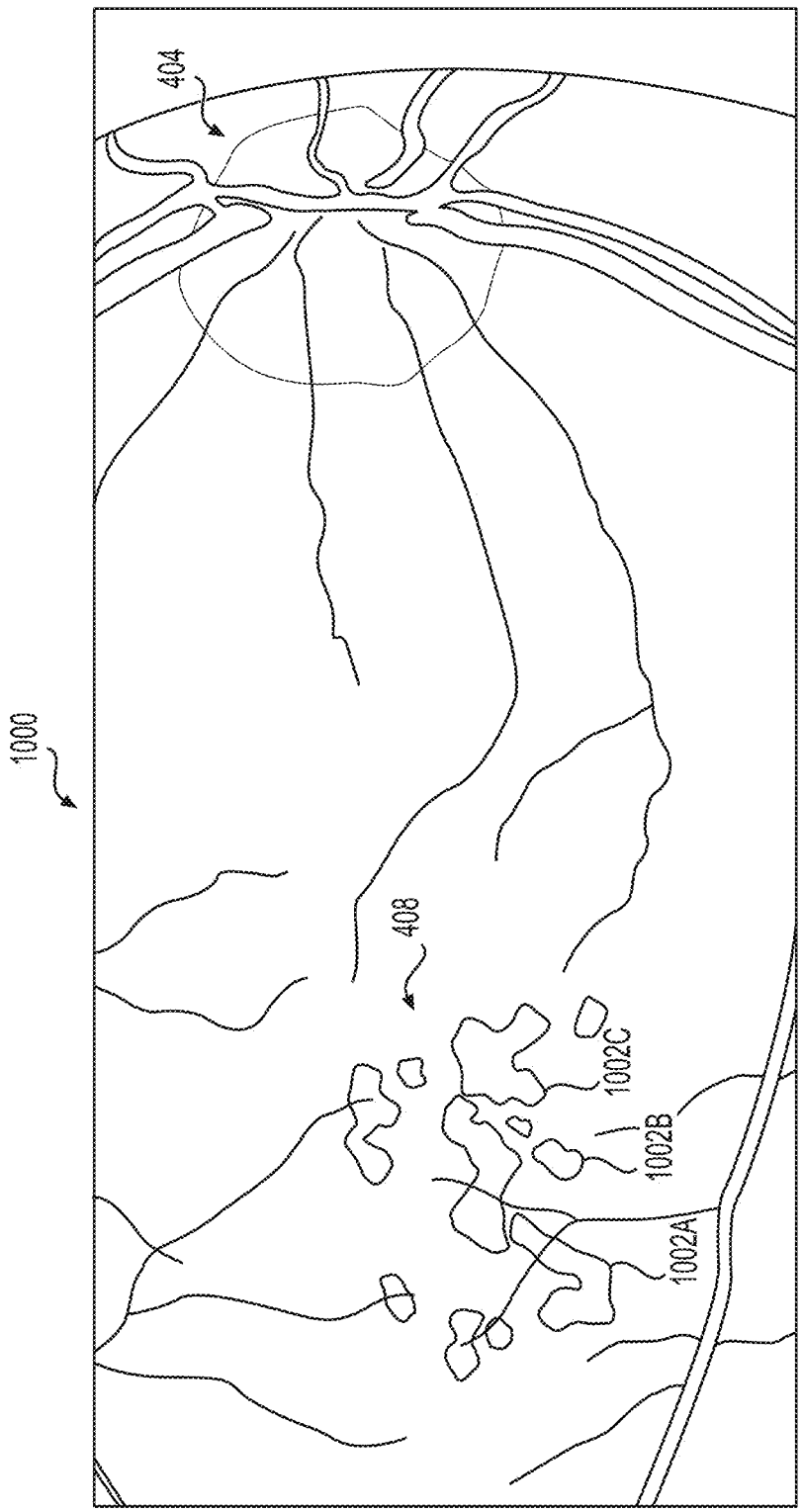
FIG. 10 illustrates still another example image of the portion of the eye shown in FIG. 4.

Moreover, FIG. 10 illustrates an additional augmented image 1000 in which a plurality of components (e.g., contours 1002A, 1002B, 1002C) representing the configurations and/or other characteristics (e.g., the shape, size, area, perimeter, location, opacity, color, etc.) of drusen disposed proximate the macula 408 are shown. As noted above, the contours and/or other components shown in any of the augmented images 804, 904, 1000 described herein may assist an ophthalmologist or other user 102 in identifying drusen (e.g., soft drusen) with greater accuracy, and may potentially assist the user 102 in diagnosing macular degeneration (e.g., age-related macular degeneration) at an earlier stage. Any of the augmented images 804, 904, 1000 described herein may comprise the image 400 obtained at 302 with one or more of the contours and/or other components described above added thereto so as to be visible to the user 102 when the augmented images 804, 904, 1000 are displayed and/or otherwise output by the vision screening device 104. At any of the steps included in the method 300, the controller 132 may cause the display 134 and/or the display 136 of the vision screening device 104 to display any of the images described above with respect to FIGS. 4-10. Additionally or alternatively, the controller 132 may provide one or more such images and/or the results of the macular degeneration screening to the vision screening system 110 via the network 108.

At 318, the controller 132 and/or one or more processors associated therewith may generate one or more lists identifying each of the plurality of contours and/or other components illustrated in the augmented image generated at 316. Such an example list may comprise a contour list may identifying and/or including a plurality of points, and each point may indicate a spatial location (e.g., longitude, latitude, a pixel, etc.) of a respective one of the contours. In other examples, such a list may identify and/or include a plurality of points or other indicia indicating a spatial location of a respective one of the other shapes, arrows, visual indicia, and/or other components included in the augmented image generated at 316. Such spatial locations may comprise locations in the augmented image. Additionally or alternatively, such spatial locations may comprise coordinates and/or other locations in the eye of the patient 106. For example, each point included in a contour list generated at 318 may indicate a spatial location of a centerpoint of a respective one of the contours included in the augmented image generated at 316. In a further example, each point included in the contour list may indicate a spatial location of a centroid of a respective one of the contours. In still further examples, each entry in the contour list may indicate a plurality of points identifying and/or located along a perimeter of a respective one of the contours. In such examples, each entry in the contour list may identify the quantity and/or characteristics (e.g., the shape, size, area, perimeter, location, opacity, color, etc.) of drusen indicated by the respective one of the contours. In some examples, each entry of the contour list generated at 318 may also indicate the brightness, sharpness, contrast, and/or other characteristics of the respective contour shown in the augmented image, as well as any of the threshold values and/or threshold areas associated with the respective contour as described above with respect to steps 304-316. In any of the examples described herein, each entry of the contour list generated at 318 may also include and/or otherwise identify the determined area of the respective contour (e.g., as determined by the controller 132 at 314), the color or hue of the drusen represented/indicated by the respective contour, a distance between the drusen indicated by the respective contour and the macula 408, a distance between the drusen indicated by the respective contour and the fovea 410, and/or an identifier (e.g., a name, a number, an alphanumeric code, etc.) uniquely identifying the respective contour or the corresponding drusen.

At 318, the controller 132 and/or one or more processors associated therewith may also store the list generated at 316 for future reference. For example, the controller 132 may store a contour list, generated at 316, locally in the computer-readable media 204 in association with the patient ID and/or other patient data noted above. Additionally or alternatively, at 318 the controller 132 may provide the contour list to the vision screening system 110, via the network 108, for storage in the computer-readable media 116. In any of the examples described herein, the contour list generated at 318 may include a timestamp and/or other metadata indicating the date, time, and/or location at which the contour list was generated. Such stored contour lists may be used by the user 102 during future macular degeneration screenings with the patient 106 to track the progress of macular degeneration.

Based at least on the description herein, it is understood that the systems and methods of the present disclosure may be used to assist in performing one or more macular degeneration screenings or other vision tests. For example, components of the systems described herein may be configured to obtain images of a patient's eye, process the various images to identify the optic disc and a region of interest associated with the macula, and to generate one or more corresponding augmented images of the eye. Such augmented images may include one or more contours or other identifiers illustrating the shape and location of drusen disposed proximate the macula. The components of the systems described herein may also be configured to generate and store one or more contour lists identifying the configurations of the respective contours shown in the augmented image.

As a result, the systems and methods described herein may assist a user 102 with identifying drusen that may not be easily identified through manual human review of the obtained images. The systems and methods described herein may, thus, reduce the volume of fundus images that a user 102 may need to review for a particular patient 106 while increasing the user's ability to correctly identify drusen in such images. The systems and methods described herein may also enable the user 102 to track the progression of macular degeneration in the patient 106 over time by generating, storing, and/or monitoring contour lists that indicate the identified drusen with particularity. Further, the systems and methods may employ artificial intelligence, machine learning, neural networks, and/or other technologies as part of any of the steps described in the method 300. The use of such technologies or techniques may further improve the ability of the system 100 to identify the early-stage formation of drusen, and to assist in monitoring the progression of macular degeneration in the patient 106.

For example, as part of the method 300 the controller 132 and/or one or more processors associated therewith may determine one or more values associated with a characteristic of the identified drusen. Such a value may comprise, for example, an area (e.g., in pixels, etc.) of drusen indicated by a particular one of the contours described above. Such a value may also comprise, for example, a color value indicating the color of the drusen, a distance between the drusen and the macula (e.g., between a centerpoint of the drusen and the centerpoint of the macula 408), etc. In such examples, the controller 132 may compare the determined value to a static or dynamic threshold associated with the characteristic. For example, the controller 132 may compare the determined value to a previous value (e.g., a previous area) determined during a previous macular degeneration screening and associated with the same drusen. Additionally or alternatively, the controller 132 may compare the determined value to an area threshold indicative of a largest permissible/acceptable drusen area. In any of the examples described herein, such a threshold may be selected and/or modified by the user 102. In such examples, if the controller 132 determines that the determined value exceeds the threshold value associated with the characteristic, the controller 132 may generate an alert based at least in part on determining that the determined value exceeds the threshold value. The controller 132 may also cause the alert to be output via the display 134 and/or may provide the alert to the vision screening system 110 via the network 108.

Additionally or alternatively, as part of the method 300, the controller 132 and/or one or more processors associated therewith may determine a first value associated with the identified drusen and based at least in part on the image 400 obtained/received at 302. In such examples, the first value may be indicative of a characteristic of the drusen (e.g., an area, a distance between the drusen and the macula 408, a color of the drusen, etc.) at a first time (e.g., on a first day, on a first date, at a particular time of day, etc.). In such examples, the controller 132 may also determine a second value associated with the same drusen and based at least in part on an additional image of the eye. In such examples, the second value may be indicative of the characteristic of the drusen at a second time later than the first time. The controller 132 may determine a difference between the first value and the second value. If the controller 132 determines that the difference between the first value and the second value exceeds a threshold value (e.g., a threshold difference indicative of an acceptable amount of change in the characteristic), the controller 132 may generate an alert based at least in part on determining that the difference exceeds the threshold value. In any of the examples described herein, such a threshold difference may be selected and/or modified by the user 102. The controller 132 may also cause the alert to be output via the display 134 and/or may provide the alert to the vision screening system 110 via the network 108.

The foregoing is merely illustrative of the principles of this disclosure and various modifications can be made by those skilled in the art without departing from the scope of this disclosure. The above described examples are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process limitations (e.g., dimensions, configurations, components, process step order, etc.) can be made to further optimize the provided structures, devices and methods, as shown and described herein. In any event, the structures and devices, as well as the associated methods, described herein have many applications. Therefore, the disclosed subject matter should not be limited to any single example described herein, but rather should be construed in breadth and scope in accordance with the appended claims.

What is claimed is:

1. A system, comprising:
a vision screening device having at least one sensor; and
a controller operably connected to the at least one sensor, the controller being configured to:
cause the at least one sensor to obtain an image of an eye;
identify, based at least in part on the image, an optic disc of the eye;
generate, at a first location, a first geometric shape approximating the optic disc, the first geometric shape having a dimension;
identify, based at least in part on the image, a region of interest exclusive of the optic disc, wherein:
the region of interest is represented by a second geometric shape disposed at a second location different from the first location, and
the second location of the second geometric shape is determined based at least in part on the dimension of the first geometric shape;
identify, based at least in part on the image, drusen disposed proximate a macula of the eye and at least partially within the region of interest;
determine a value indicative of a characteristic of the drusen; and
generate an alert based at least in part on the value exceeding a threshold.

2. The system of claim 1, wherein the characteristic of the drusen comprises at least one of an area, a color, an opacity, and a distance between the drusen and the macula.

3. The system of claim 1, the vision screening device further comprising computer-readable media storing one or more macular degeneration screening components configured to assist in generating an augmented image of the eye, the augmented image including a component indicating the drusen.

4. The system of claim 3, wherein the component comprises a contour identifying at least part of a perimeter of the drusen.

5. The system of claim 1, wherein the controller is further configured to:
identify, using the image, a plurality of contours associated with the optic disc; and
position the first geometric shape such that a centerpoint of the first geometric shape overlays a centroid corresponding to the plurality of contours.

6. The system of claim 5, wherein
the first geometric shape comprises a circle,
the dimension of the first geometric shape comprises a radius of the circle; and
the centroid comprises:
a centroid of a largest contour included in the plurality of contours, or
a cumulative centroid of the plurality of contours.

7. The system of claim 5, wherein the controller is further configured to identify a dimension of the second geometric shape representing the region of interest based at least in part on the dimension of the first geometric shape,
a centerpoint of the second geometric shape is spaced from the centerpoint of the first geometric shape by a distance, and
the distance is determined based at least in part on the dimension of the first geometric shape.

8. The system of claim 1, wherein identifying the drusen comprises applying a contrast limited adaptive histogram equalization to image data captured by a single channel of the at least one sensor, the image data corresponding to the image of the eye.

9. The system of claim 8, wherein identifying the drusen further comprises applying a brightness threshold to at least part of the image data.

10. The system of claim 9, wherein identifying the drusen further comprises applying an area threshold to at least part of the image data.

11. The system of claim 10, wherein generating the augmented image comprises generating the component based at least in part on image data satisfying the area threshold.

12. The system of claim 1, wherein the second geometric shape is different from the first geometric shape.

13. The system of claim 1, further comprising:
a display operably connected to the controller and configured to display an augmented image of the eye, the augmented image including a component indicating the drusen, and
a vision screening system operably connected to the vision screening device via a network, wherein the controller is configured to:
generate a list identifying a distance between the drusen and the macula, and
provide the list to the vision screening system via the network.

14. The system of claim 1, wherein the controller is configured to determine the second location of the second geometric shape, relative to the first location of the first geometric shape, based on the dimension of the first geometric shape.

15. The system of claim 1, wherein determining the second location of the second geometric shape comprises determining a location of a centerpoint of the second geometric shape based on the first dimension of the first geometric shape.

16. A method, comprising:
receiving, with a controller, an image of an eye;
identifying, with the controller and based at least in part on the image, an optic disc of the eye;
identifying, with the controller a first geometric shape corresponding to the optic disc, the first geometric shape being disposed at a first location and having a dimension;
identifying, with the controller, a region of interest exclusive of the optic disc, wherein:
the region of interest is represented by a second geometric shape disposed at a second location different from the first location, and
the second location of the second geometric shape is determined based at least in part on the dimension of the first geometric shape;
identifying, with the controller and based at least in part on the image, drusen disposed at least partially within the region of interest; and
generating, with the controller, an augmented image of the eye, the augmented image including a component indicating the drusen.

17. The method of claim 16, further comprising generating, with the controller, a list identifying at least one of a location of the drusen indicated by the component, a perimeter of the drusen indicated by the component, and a color of the drusen indicated by the component.

18. The method of claim 16, wherein identifying the drusen comprises at least one of:
applying a contrast limited adaptive histogram equalization to image data captured by a single channel of an image capture device,
applying a brightness threshold to at least part of the image data, and
applying an area threshold to at least part of the image data.

19. A system, comprising:
a controller; and
memory storing instructions which, when executed by the controller, cause the controller to perform operations including:
receiving an image of an eye,
identifying, based at least in part on the image, an optic disc of the eye;
generate, at a first location, a first geometric shape associated with the optic disc;
identify a region of interest of the eye exclusive of the optic disc, wherein:
the region of interest is represented by a second geometric shape disposed at a second location different from the first location, and
the second location of the second geometric shape is determined based at least in part on a dimension of the first geometric shape;
identifying, based at least in part on the image, drusen disposed at least partially within the region of interest; and
generating an augmented image of the eye, the augmented image including a component indicating the drusen.

20. The system of claim 19, wherein the operations further include causing a display to display the augmented image of the eye,
the component comprising a contour identifying at least part of a perimeter of the drusen.

21. The system of claim 19, wherein the image comprises a fundus image captured by a vision screening device, and the controller comprises a controller of a vision screening system operably connected to the vision screening device.

22. The system of claim 19, wherein the operations further include:
determining a value associated with a characteristic of the drusen,
determining that the value exceeds a threshold value associated with the characteristic, and
generating an alert based at least in part on determining that the value exceeds the threshold value.

23. The system of claim 22, wherein the characteristic of the drusen comprises at least one of an area, a color, an opacity, and a distance between the drusen and a macula of the eye.

24. The system of claim 19, wherein the operations further include:
determining a first value associated with the drusen and based at least in part on the image, the first value being indicative of a characteristic of the drusen at a first time, determining a second value associated with the drusen and based at least in part on an additional image of the eye, the second value being indicative of the characteristic of the drusen at a second time later than the first time, determining a difference between the first value and the second value, determining that the difference exceeds a threshold value, generating an alert based at least in part on determining that the difference exceeds the threshold value; and causing a device to output the alert.

* * * * *